US008324344B2

(12) United States Patent
Kisiel

(10) Patent No.: US 8,324,344 B2
(45) Date of Patent: Dec. 4, 2012

(54) MEMBRANE TRANSDUCTION PEPTIDES AND METHODS OF DELIVERING MATERIAL TO A TARGET CELL

(75) Inventor: Walter Kisiel, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 13/129,942

(22) PCT Filed: Oct. 7, 2009

(86) PCT No.: PCT/US2009/059849
§ 371 (c)(1),
(2), (4) Date: Aug. 8, 2011

(87) PCT Pub. No.: WO2010/074794
PCT Pub. Date: Jul. 1, 2010

(65) Prior Publication Data
US 2011/0286934 A1    Nov. 24, 2011

Related U.S. Application Data

(60) Provisional application No. 61/122,600, filed on Dec. 15, 2008, provisional application No. 61/149,180, filed on Feb. 2, 2009.

(51) Int. Cl.
| | |
|---|---|
| A61K 38/00 | (2006.01) |
| A61K 38/04 | (2006.01) |
| A61K 9/127 | (2006.01) |
| A61K 38/10 | (2006.01) |
| A61K 38/08 | (2006.01) |
| A61K 38/06 | (2006.01) |
| A61K 38/07 | (2006.01) |
| C07K 5/00 | (2006.01) |
| C07K 16/00 | (2006.01) |
| C07K 17/00 | (2006.01) |
| C07K 7/00 | (2006.01) |
| A61B 5/00 | (2006.01) |
| A61B 8/00 | (2006.01) |
| A61B 10/00 | (2006.01) |

(52) U.S. Cl. .......... 530/326; 424/9.6; 424/450; 514/1.1; 514/21.5; 514/21.6; 514/21.7; 514/21.8; 514/21.9; 530/327; 530/328; 530/329; 530/330; 530/350

(58) Field of Classification Search ........................ None
See application file for complete search history.

(56) References Cited

U.S. PATENT DOCUMENTS

| | | | | |
|---|---|---|---|---|
| 5,563,123 | A * | 10/1996 | Innis et al. | 514/14.9 |
| 5,981,471 | A | 11/1999 | Papathanassiu et al. | |
| 6,783,960 | B2 | 8/2004 | Innis et al. | |
| 7,432,238 | B2 | 10/2008 | Kisiel et al. | |
| 7,745,391 | B2 * | 6/2010 | Mintz et al. | 514/19.3 |
| 2009/0099087 | A1 * | 4/2009 | Kisiel et al. | 514/12 |

OTHER PUBLICATIONS

Chiesa A, et al. Biochem J. 355:1-12, 2001.*
International Search Report and Written Opinion mailed Jun. 21, 2010 in related PCT Application No. PCT/US2009/059849; 9 pgs.
International Preliminary Report on Patentability mailed Jun. 21, 2011 in related PCT Application No. PCT/US2009/059849; 6 pgs.
Annand et al., "Caspase-1 (interleukin-1β-converting enzyme) is inhibited by the human serpin analogue proteinase inhibitor 9," *Biochem. J.*, Sep. 15, 1999; 342(Pt. 3): 655-65.
Arepally et al., "Characterization of a murine monoclonal antibody that mimics heparin-induced thrombocytopenia antibodies," *Blood*, Mar. 1, 2000; 95(5): 1533-40.
Bailey et al., "Characterization of the Localization and Proteolytic Activity of the SUMO-specific Protease, SENP1,"*J. Biol. Chem.*, Jan. 2, 2004; 279(1): 692-703. Available online Oct. 16, 2003.
Bird et al., "Nucleocytoplasmic Distribution of the Ovalbumin Serpin PI-9 Requires a Nonconventional Nuclear Import Pathway and the Export Factor Crml," *Mol. Cell. Biol.*, Aug. 2001; 21(16): 5396-407.
Chand et al., "The effect of human tissue factor pathway inhibitor-2 on the growth and metastasis of fibrosarcoma tumors in athymic mice," *Blood*, Feb. 1, 2004; 103(3): 1069-77. Available online Oct. 2, 2003.
Chand et al., "Structure-Function Analysis of the Reactive Site in the First Kunitz-type Domain of Human Tissue Factor Pathway Inhibitor-2," *J. Biol. Chem.*, Apr. 23, 2004; 279(17): 17500-7. Available online Feb. 16, 2004.
Chand et al., "Structure, function and biology of tissue factor pathway inhibitor-2," *Thromb. Haemost.*, Dec. 2005; 94(6): 1122-30.
Chand et al., "Identification of a novel human tissue factor splice variant that is upregulated in tumor cells," *Int. J. Cancer.*, Apr. 1, 2006; 118(7): 1713-20.
Chen et al., "Degredation of DNA Topoisomerase I by a Novel Trypsin-like Serine Protease in Proliferating Human T Lymphocytes," *J. Biol. Chem.*, Apr. 28, 2000; 275(17): 13109-17.
Chuang et al., "Identification of a Nuclear Targeting Domain in the Insertion between Helices C and D in Protease Inhibitor-10,"*J. Biol. Chem.*, Apr. 16, 1999; 274(16): 11194-8.
Derossi et al., "The Third Helix of the Antennapedia Homeodomain Translocates through Biological Membranes," *J. Biol. Chem.*, Apr. 8, 1994; 269(14): 10444-50.
Derossi et al., "Cell Internalization of the Third Helix of the Antennapedia Homeodomain Is Receptor-independent," *J. Biol. Chem.*, Jul. 26, 1996; 271(30): 18188-93.

(Continued)

*Primary Examiner* — Robert Landsman
(74) *Attorney, Agent, or Firm* — Mueting Raasch & Gebhardt, P.A.

(57) ABSTRACT

Isolated polypeptides, nucleic acids, and methods relating to cellular internalization of materials are described herein. Generally, the isolated polypeptides include a membrane transduction domain of human tissue factor pathway inhibitor-2 (TFPI-2). In some cases, the isolated polypeptide can be a fusion peptide that includes a membrane transduction domain of human TFPI-2 and a heterologous peptide domain. The nucleic acids include nucleic acids that encode the isolated polypeptides described herein. The methods generally include providing a composition that includes a membrane transduction domain of human TFPI-2 coupled to a material, and contacting the composition with a cell under conditions effective to permit the cell to internalize the composition.

22 Claims, 8 Drawing Sheets

OTHER PUBLICATIONS

Du et al., "Human tissue factor pathway inhibitor-2 does not bind or inhibit activated matrix metalloproteinase-1," *Biochim. Biophys. Acta*, Jun. 11, 2003; 1621(3): 242-5.

Du et al., "Molecular cloning, expression, and characterization of bovine tissue factor pathway inhibitor-2," *Arch. Biochem. Biophys.*, Sep. 1, 2003; 417(1): 96-104.

Frankel et al., "Cellular uptake of the tat protein from human immunodeficiency virus," *Cell*, Dec. 23, 1988; 55(6): 1189-93.

Goldfarb et al., "Importin alpha: a multipurpose nuclear-transport receptor," *Trends Cell Biol.*, Sep. 2004;14(9): 505-14.

Guo et al., "Intracellular distribution of the lysyl oxidase propetide in osteoblastic cells," *Am. J. Physiol. Cell Physiol.*, Jun. 2007; 292(6): C2095-102. Available online Feb. 7, 2007.

Herman et al., "Tissue factor pathway inhibitor-2 is a novel inhibitor of matrix metalloproteinases with implications for atherosclerosis," *J. Clin. Invest.*, May 2001; 107(9): 1117-26.

Hisaka et al., "cDNA cloning and tissue distribution of the rat ortholog of tissue factor pathway inhibitor-2," *Thromb. Haemost.*, Aug. 2002; 88(2): 356-7.

Hisaka et al., "Expression of tissue factor pathway inhibitor-2 in murine and human liver regulation during inflammation," *Thromb. Haemost.*, Mar. 2004; 91(3): 569-75.

Iino et al., "Quantification and Characterization of Human Endothelial Cell-Derived Tissue Factor Pathway Inhibitor-2," *Arterioscler. Thromb. Vasc. Biol.*, Jan. 1998;18(1): 40-6.

Kempaiah et al., "Identification of a human TFPI-2 splice variant that is upregulated in human tumor tissues," *Mol. Cancer*, Mar. 12, 2007; 6: 20, 11 pgs.

Kempaiah et al., "Human tissue factor pathway inhibitor-2 induces caspase-mediated apoptosis in a human fibrosarcoma cell line," *Apoptosis*, May 2008; 13(5): 702-15.

Kempaiah et al., "Human tissue factor pathway inhibitor-2 is internalized by cells and translocated to the nucleus by the importin system," *Arch. Biochem. Biophys.*, Feb. 2009; 482(1-2): 58-65. Available online Dec. 10, 2008.

Kisiel, Grant Abstract, Grant Number: 5RO1HL064119-01A1 [online]. National Heart, Lung and Blood Institute, project dates: Sep. 5, 2000 to Jul. 31, 2004 [retrieved on Aug. 26, 2011]. Retrieved from the Internet: <URL: http://projectreporter.nih.gov/project_info_description.cfm?aid=6195834&icde=0>, 1 pg.

Konduri et al., "A novel function of tissue factor pathway inhibitor-2 (TFPI-2) in human glioma invasion," *Oncogene*, Oct. 18, 2001; 20(47): 6938-45.

Konduri et al., "Minimal and inducible regulation of tissue factor pathway inhibitor-2 in human gliomas," *Oncogene*, Jan. 31, 2002; 21(6): 921-8.

Konduri et al., "Promoter methylation and silencing of the tissue factor pathway inhibitor-2 (TFPI-2), in human glioma cells," *Oncogene*, Jul. 17, 2003; 22(29): 4509-16.

Kuninaka et al., "Serine protease Omi/HtrA2 targets WARTS kinase to control cell proliferation," *Oncogene*, Apr. 12, 2007; 26(17): 2395-406. Available online Nov. 20, 2006.

Marioni et al., "Nuclear localization of mammary serine protease inhibitor (MASPIN): is its impact on the prognosis in laryngeal carcinoma due to a proapoptotic effect?" *Am. J. Otolaryngol.*, May-Jun. 2008; 29(3): 156-62. Available online Mar. 17, 2008.

Meyer et al., "Carboxyl-Truncated STAT5βIs Generated by a Nucleus-Associated Serine Protease in Early Hematopoietic Progenitors," *Blood*, Mar. 15, 1998; 91(6): 1901-8.

Mi et al., "Characterization of a Class of Cationic Peptides Able to Facilitate Efficient Protein Transduction in Vitro and in Vivo," *Mol. Therapy*, Oct. 2000; 2(4): 339-47.

Neaud et al., "Thrombin Up-regulates Tissue Factor Pathway Inhibitor-2 Synthesis through a Cyclooxygenase-2-dependent, Epidermal Growth Factor Receptor-independent Mechanism," *J. Biol. Chem.*, Feb. 13, 2004; 279(7): 5200-6. Available online Nov. 17, 2003.

Nishibori et al., "Localization of a serine proteinase inhibitor, B-43, in the bovine pancreas," *Histochem. Cell Biol.*, 1998; 110(1): 51-6.

Planque, "Nuclear trafficking of secreted factors and cell-surface receptors: new pathways to regulate cell proliferation and differentiation, and involvement in cancers," *Cell Communication and Signaling*, Oct. 18, 2006; 4: 7, 18 pgs.

Rao et al., "Partial characterization of matrix-associated serine protease inhibitors from human skin cells," *J. Invest. Dermatol.*, Mar. 1995; 104(3): 379-83.

Rao et al., "Regulation of ProMMP-1 and ProMMP-3 activation by tissue factor pathway inhibitor-2/matrix-associated serine protease inhibitor," *Biochem. Biophys. Res. Commun.*, Feb. 5, 1999; 255(1): 94-8.

Schmidt et al., "Crystal Structure of Kunitz Domain 1 (KD1) of Tissue Factor Pathway Inhibitor-2 in Complex with Trypsin: Implications for KD1 Specificity of Inhibition," *J. Biol. Chem.*, Jul. 29, 2005; 280(30): 27832-8. Available online Jun. 2, 2005.

Scholtz et al., "Appearance of nuclear protease activity after embryonal carcinoma cells undergo differentiation," Dev. Biol., Feb. 1, 1996; 173(2): 420-7.

Sierko et al., "The role of tissue factor pathway inhibitor-2 in cancer biology," *Semin. Thromb. Hemost.*, Oct. 2007; 33(7): 653-9.

Sprecher et al., "Molecular cloning, expression, and partial characterization of a second human tissue-factor-pathway inhibitor," *Proc. Natl. Acad. Sci. USA*, Apr. 12, 1994; 91(8): 3353-7.

Stepanova et al., "Nuclear translocation of urokinase-type plasminogen activator," *Blood*, Jul. 1, 2008; 112(1): 100-10. Available online Mar. 12, 2008.

Strik et al., "Distribution of the Human Intracellular Serpin Protease Inhibitor 8 in Human Tissues," *J. Histochem. Cytochem.*, Nov. 2002; 50(11): 1443-53.

Sugiyama et al., "cDNA macroarray analysis of gene expression in synoviocytes stimulated with TNFalpha," *FEBS Lett.*, Apr. 24, 2002; 517(1-3): 121-8.

Tatusova et al., "BLAST 2 Sequences, a new tool for comparing protein and nucleotide sequences," *FEMS Microbiol. Lett.*, May 15, 1999; 174(2): 247-50.

Ter-Avetisyan et al., "Cell Entry of Arginine-rich Peptides Is Independent of Endocytosis," *J. Biol. Chem.*, Feb. 6, 2009; 284(6): 3370-8. Available online Dec. 1, 2008.

Thompson et al., "CLUSTAL W: improving the sensitivity of progressive multiple sequence alignment through sequence weighting, position-specific gap penalties and weight matrix choice," *Nucl. Acids. Res.*, Nov. 11, 1994; 22(22): 4673-80.

Trapani et al., "Localization of Granzyme B in the Nucleus: A Putative Role in the Mechanism of Cytotoxic Lymphocyte-Mediated Apoptosis," *J. Biol. Chem.*, Feb. 23, 1996; 271(8): 4127-33.

Wojtukiewicz et al., "Immunohistochemical localization of tissue factor pathway inhibitor-2 in human tumor tissue," *Thromb. Haemost.*, Jul. 2003; 90(1): 140-6.

Xu et al., "Tissue Factor Pathway Inhibitor-2 is Upregulated by Vascular Endothelial Growth Factor and Suppresses Growth Factor-Induced Proliferation of Endothelial Cells," *Arterioscler. Thromb. Vasc. Biol.*, Dec. 2006; 26(12): 2819-25. Available online Oct. 5, 2006.

* cited by examiner

Figure 5A.
Figure 5B.
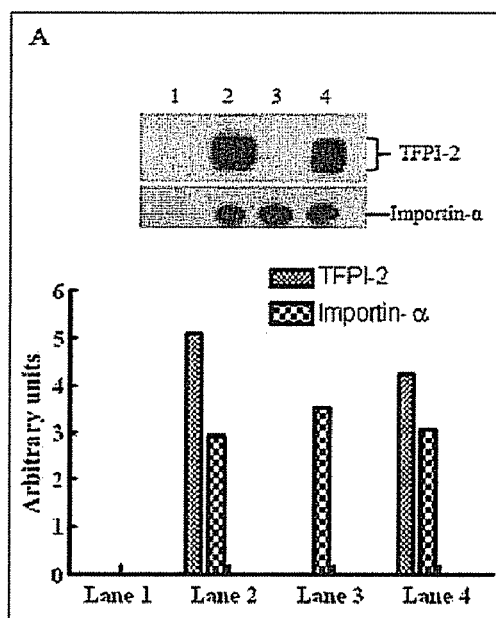
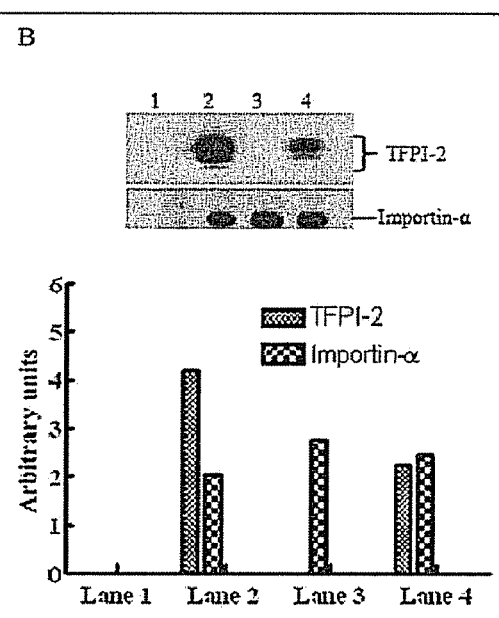

Figure 6

DAAQEPTGNNAEICLLPLDYGPCRALLLRYYYDRYTQSCRQFLYGGCEGNAN
NFYTWEACDDACWRIEKVPKVCRLQVSVDDQCEGSTEKYFFNLSSMTCEKFF
SGGCHRNRIENRFPDEATCMGFCAPKKIPSFCYSPKDEGLCSANVTRYYFNPR
YRTCDAFTYTGCGGNDNNFVSREDCKRACAKALKKKKKMPKLRFASRIRKI
RKKQF (SEQ ID NO:1)

Figure 7

DAAQEPTGNNAEICLLPLDYGPCRALLLRYYYDRYTQSCRQFLYGGCEGNAN
NFYTWEACDDACWRIEKVPKVEFAKALKKKKKMPKLRFASRIRKIRKKQF
(SEQ ID NO:2)

SEQUENCE LISTING

```
<160> NUMBER OF SEQ ID NOS: 2

<210> SEQ ID NO 1
<211> LENGTH: 213
<212> TYPE: PRT
<213> ORGANISM: Homo sapiens
<220> FEATURE:
<221> NAME/KEY: MISC_FEATURE
<223> OTHER INFORMATION: tissue factor pathway inhibitor-2
```

<400> SEQUENCE: 1

```
Asp Ala Ala Gln Glu Pro Thr Gly Asn Asn Ala Glu Ile Cys Leu Leu
1               5                   10                  15
Pro Leu Asp Tyr Gly Pro Cys Arg Ala Leu Leu Arg Tyr Tyr Tyr
            20                  25                  30
Asp Arg Tyr Thr Gln Ser Cys Arg Gln Phe Leu Tyr Gly Gly Cys Glu
            35                  40                  45
Gly Asn Ala Asn Asn Phe Tyr Thr Trp Glu Ala Cys Asp Asp Ala Cys
        50                  55                  60
Trp Arg Ile Glu Lys Val Pro Lys Val Cys Arg Leu Gln Val Ser Val
65                  70                  75                  80
Asp Asp Gln Cys Glu Gly Ser Thr Glu Lys Tyr Phe Phe Asn Leu Ser
                85                  90                  95
Ser Met Thr Cys Glu Lys Phe Phe Ser Gly Gly Cys His Arg Asn Arg
            100                 105                 110
Ile Glu Asn Arg Phe Pro Asp Glu Ala Thr Cys Met Gly Phe Cys Ala
            115                 120                 125
Pro Lys Lys Ile Pro Ser Phe Cys Tyr Ser Pro Lys Asp Glu Gly Leu
            130                 135                 140
Cys Ser Ala Asn Val Thr Arg Tyr Tyr Phe Asn Pro Arg Tyr Arg Thr
145                 150                 155                 160
Cys Asp Ala Phe Thr Tyr Thr Gly Cys Gly Gly Asn Asp Asn Asn Phe
                165                 170                 175
Val Ser Arg Glu Asp Cys Lys Arg Ala Cys Ala Lys Ala Leu Lys Lys
            180                 185                 190
Lys Lys Lys Met Pro Lys Leu Arg Phe Ala Ser Arg Ile Arg Lys Ile
            195                 200                 205
Arg Lys Lys Gln Phe
        210
```

<210> SEQ ID NO 2
<211> LENGTH: 102
<212> TYPE: PRT
<213> ORGANISM: artificial
<220> FEATURE:
<223> OTHER INFORMATION: chimera of the first Kunitz-type domain (with the R24K mutation) and the carboxy-terminal tail

<400> SEQUENCE: 2

```
Asp Ala Ala Gln Glu Pro Thr Gly Asn Asn Ala Glu Ile Cys Leu Leu
1               5                   10                  15
Pro Leu Asp Tyr Gly Pro Cys Arg Ala Leu Leu Arg Tyr Tyr Tyr
            20                  25                  30
Asp Arg Tyr Thr Gln Ser Cys Arg Gln Phe Leu Tyr Gly Gly Cys Glu
            35                  40                  45
Gly Asn Ala Asn Asn Phe Tyr Thr Trp Glu Ala Cys Asp Asp Ala Cys
        50                  55                  60
Trp Arg Ile Glu Lys Val Pro Lys Val Glu Phe Ala Lys Ala Leu Lys
65                  70                  75                  80
Lys Lys Lys Lys Met Pro Lys Leu Arg Phe Ala Ser Arg Ile Arg Lys
                85                  90                  95
Ile Arg Lys Lys Gln Phe
            100
```

US 8,324,344 B2

MEMBRANE TRANSDUCTION PEPTIDES AND METHODS OF DELIVERING MATERIAL TO A TARGET CELL

CROSS-REFERENCE TO RELATED APPLICATION

This application is the §371 U.S. National Stage of International Application No. PCT/US2009/059849, filed 7 Oct. 2009, which claims priority to U.S. Provisional Patent Application Ser. No. 61/122,600, filed Dec. 15, 2008 and U.S. Provisional Patent Application Ser. No. 61/149,180, filed Feb. 2, 2009, each of which is incorporated by reference herein in its entirety.

STATEMENT OF GOVERNMENT RIGHTS

This invention was made with government support under a grant from the National Institutes of Health, Grant No. HL 64119. The U.S. government has certain rights in this invention.

BACKGROUND

Human tissue factor pathway inhibitor-2 (TFPI-2), a 32 kDa Kunitz-type serine proteinase inhibitor, is primarily synthesized and secreted into the extracellular matrix (ECM) by a wide variety of cells including keratinocytes, dermal fibroblasts, endothelial cells, smooth muscle cells, and synoviocytes. Several lines of evidence suggest that TFPI-2 regulates the plasmin-mediated activation of matrix pro-metalloproteinases and plays a significant role in the regulation of ECM degradation, which is an essential step for tumor cell invasion and metastasis. TFPI-2, as well as a mutated first Kunitz-type domain (R24K KD1), also has been shown to induce caspase-mediated apoptosis in several tumor cell lines.

SUMMARY OF THE INVENTION

In one aspect, the present invention provides an isolated polypeptide that includes a membrane transduction peptide of human tissue factor pathway inhibitor-2 (TFPI-2). The membrane transduction peptide can include an amino acid sequence having at least 80% similarity to at least five contiguous amino acids from amino acids 191-211 of SEQ ID NO:1, with the proviso that the isolated polypeptide is not the complete human TFPI-2 polypeptide (SEQ ID NO:1). In other embodiments, the membrane transduction peptide can include an amino acid sequence having at least 80% similarity to at least five contiguous amino acids from amino acids 187-213 of SEQ ID NO:1.

In another aspect, the isolated polypeptide can be a fusion polypeptide that includes at least two domains. One domain is a membrane transduction domain that includes a membrane transduction peptide of human tissue factor pathway inhibitor-2 (TFPI-2). A second domain is a heterologous polypeptide domain—i.e., a heterologous (i.e., non-TFPI-2) polypeptide.

In some embodiments, the membrane transduction peptide of the isolated polypeptide can include an amino acid sequence having at least 80% similarity to one or more of the following amino acid sequences: amino acids 186-195 of SEQ ID NO:1, amino acids 186-198 of SEQ ID NO:1, amino acids 187-195 of SEQ ID NO:1, amino acids 187-198 of SEQ ID NO:1, amino acids 191-198 of SEQ ID NO:1, amino acids 198-211 of SEQ ID NO:1, amino acids 198-213 of SEQ ID NO:1, amino acids 191-211 of SEQ ID NO:1, amino acids 188-213 of SEQ ID NO:1, amino acids 191-195 of SEQ ID NO:1 and amino acids 206-211 of SEQ ID NO:1.

In another aspect, the invention provides an isolated polynucleotide that includes a nucleic acid sequence that encodes a membrane transduction peptide of human tissue factor pathway inhibitor-2 (TFPI-2), wherein the membrane transduction peptide includes an amino acid sequence having at least 80% similarity to at least five contiguous amino acids from amino acids 191-211 of SEQ ID NO:1, with the proviso that the isolated polypeptide is not the complete human TFPI-2 polypeptide (SEQ ID NO:1). In other embodiments, the membrane transduction peptide encoded by the isolated polynucleotide can include an amino acid sequence having at least 80% similarity to at least five contiguous amino acids from amino acids 187-213 of SEQ ID NO:1.

In another aspect, the invention provides an isolated polynucleotide that includes a nucleic acid sequence that encodes a polypeptide that includes a membrane transduction domain comprising a membrane transduction peptide of human tissue factor pathway inhibitor-2 (TFPI-2), and a heterologous polypeptide domain.

In some embodiments, the membrane transduction peptide encoded by the polynucleotide can include an amino acid sequence having at least 80% similarity to one or more of the following amino acid sequences: amino acids 186-195 of SEQ ID NO:1, amino acids 186-198 of SEQ ID NO:1, amino acids 187-195 of SEQ ID NO:1, amino acids 187-198 of SEQ ID NO:1, amino acids 191-198 of SEQ ID NO:1, amino acids 198-211 of SEQ ID NO:1, amino acids 198-213 of SEQ ID NO:1, amino acids 191-211 of SEQ ID NO:1, amino acids 188-213 of SEQ ID NO:1, amino acids 191-195 of SEQ ID NO:1 and amino acids 206-211 of SEQ ID NO:1.

In another aspect, the present invention provides a method of delivering a material to a target cell. Generally, the method includes providing a composition comprising the material coupled to a membrane transduction domain, wherein the membrane transduction domain includes a membrane transduction peptide of human tissue factor pathway inhibitor-2 (TFPI-2), and contacting the composition with the target cell under conditions effective to permit the target cell to internalize the composition.

In some embodiments, the membrane transduction peptide of the isolated polypeptide can include an amino acid sequence having at least 80% similarity to one or more of the following amino acid sequences: amino acids 186-195 of SEQ ID NO:1, amino acids 186-198 of SEQ ID NO:1, amino acids 187-195 of SEQ ID NO:1, amino acids 187-198 of SEQ ID NO:1, amino acids 191-198 of SEQ ID NO:1, amino acids 198-211 of SEQ ID NO:1, amino acids 198-213 of SEQ ID NO:1, amino acids 191-211 of SEQ ID NO:1, amino acids 188-213 of SEQ ID NO:1, amino acids 191-195 of SEQ ID NO:1 and amino acids 206-211 of SEQ ID NO:1.

In some embodiments, the composition can be internalized to the cell cytoplasm. In other embodiments, the composition can be internalized to the cell nucleus.

In some embodiments, the material can include a biological material such as, for example, a polypeptide, a nucleic acid, or a liposome.

In some embodiments, the material can include an active agent such as, for example, a drug, a fluorophore, or a nucleic acid.

BRIEF DESCRIPTION OF THE DRAWING

FIG. 5A-5B. TFPI-2 interacts with importin-α.(A) HT-1080 cells overexpressing TFPI-2 and untransfected cells were subjected to co-immunoprecipitation using SK-9 and importin-αantibodies. The complexes were immunoblotted separately using anti-TFPI-2 and anti-importin-αantibodies. Lane 1, HT-1080 untransfected cell lysate co-immunoprecipitated with SK-9; lane 2, HT-1080 cells overexpressing TFPI-2 co-immunoprecipitated with SK-9; lane 3, HT-1080 untransfected cell lysate co-immunoprecipitated with anti-importin-α; lane 4, HT-1080 cells overexpressing TFPI-2 co-immunoprecipitated with anti-importin-α. For immunoblot analysis, the intensity of blot bands were assessed by densitometric semi-quantitation and depicted by a bar diagram (lower panel). (B) HT-1080 cells were treated with 1 μM TFPI-2 and processed for co-immunoprecipitation. The complexes were similarly immunoblotted using anti-TFPI-2 and anti-importin-αantibodies. Lane 1, lysate from vehicle treated HT-1080 cells co-immunoprecipitated with SK-9; lane 2, lysate from TFPI-2 treated HT-1080 cells co-immunoprecipitated with SK-9; lane 3, lysate from vehicle treated HT-1080 cells co-immunoprecipitated with anti-importin-α; lane 4, lysate from TFPI-2 treated HT-1080 cells co-immunoprecipitated with anti-importin-α. For immunoblot analysis, the intensity of blot bands were assessed by densitometric semi-quantitation and depicted by a bar diagram (lower panel).

FIG. 6 shows the amino acid sequence of human tissue factor pathway inhibitor-2 (TFPI-2) (SEQ ID NO:1).

FIG. 7 shows the amino acid sequence of the R24K KD1-CT polypeptide (SEQ ID NO:2).

DETAILED DESCRIPTION OF EXEMPLARY EMBODIMENTS

Figure 1A:
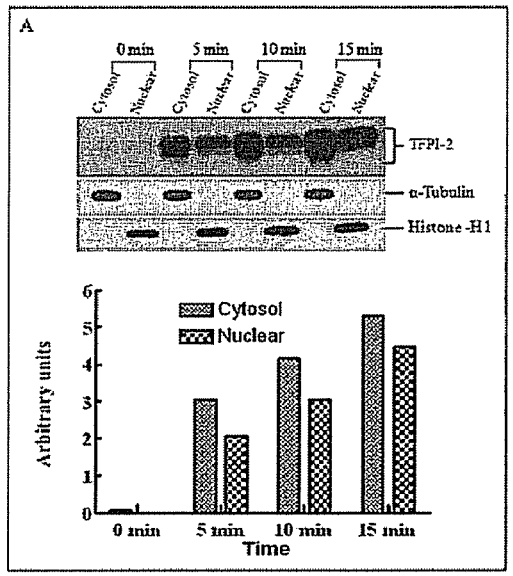
FIG. 1A-1D. Internalization of recombinant TFPI-2 protein in HT-1080cells. Cells were grown to confluence under standard conditions either in six-well plates or two-chamber culture slides. (A) Cells grown in six-well plates were treated with 1 μM TFPI-2 and incubated at 37° C. for the indicated times and harvested for fractionation. To detect the presence of offered proteins, cytosolic and nuclear fractions were probed with anti-TFPI-2antibody. The purity of cytosolic and nuclear fractions was verified using anti-α-tubulin and anti-histone-H1 antibodies, respectively. For immunoblot analysis, the intensity of blot bands were assessed by densitometric semi-quantitation and depicted by a bar diagram (lower panel). (B) Cells grown in two-chamber culture slides were incubated with either vehicle control or 50 μg/ml of Alexa Fluor-conjugated TFPI-2 at 37° C. for the indicated times and processed for confocal microscopy: (a) vehicle treated cells, (b) cells incubated with Alexa Fluor 488-conjugated TFPI-2 for five minutes, (c) cells incubated with Alexa Fluor 488-conjugated TFPI-2 for 10 minutes, and (d) cells incubated with Alexa Fluor 488-conjugated TFPI-2 for two hours. The nucleus is counterstained using DAPI in mounting media. (C) Another set of cells treated with 1 μM TFPI-2were incubated at 4° C. for the indicated times and processed for immunoblotting. For immunoblot analysis, the intensity of blot bands were assessed by densitometric semi-quantitation and depicted by a bar diagram (lower panel). (D) Cells were treated with 50 μg/ml of Alexa Fluor 488-conjugated TFPI-2, incubated at 4° C. for the indicated times, and processed for confocal microscopy: (a) vehicle treated cells, (b) cells incubated with Alexa Fluor 488-conjugated TFPI-2 for five minutes, (c) cells incubated with Alexa Fluor 488-conjugated TFPI-2 for 10 minutes, and (d) cells incubated with Alexa Fluor 488-conjugated TFPI-2 for two hours. At 4° C., Alexa Fluor 488-conjugated TFPI-2 treated cells exhibited a punctate pattern of intracellular TFPI-2 distribution. The arrows in panel (d) indicate the presence of the protein in the nucleus.

The present invention relates polypeptides useful for transporting a composition into a cell. The polypeptides include one or more membrane transduction peptides of human TFPI-2. The TFPI-2 membrane transduction peptides are naturally located at the carboxy-terminal end of the TFPI-2 polypeptide. The TFPI-2 membrane transduction peptides can promote the transfer of materials coupled to the membrane transduction peptide across a cell membrane. In some cases, a TFPI-2 membrane transduction peptide can promote the transfer of materials across the plasma membrane of a cell. In certain cases, a TFPI-2 membrane transduction peptide can promote the transfer of materials into the nucleus of the cell. The transfer across the plasma membrane of a material coupled to a TFPI-2 membrane transduction peptide can occur in a receptor-independent and/or energy-independent basis. Thus, the membrane transduction peptides described herein can be an effective tool for general delivering materials to cells.

The invention further includes polynucleotides that encode the polypeptides described herein.

Also, the invention further includes methods of delivering a material to a cell. Generally, such a method includes providing a composition that includes a membrane transduction peptide coupled to the material to be delivered to a cell, and contacting the composition with the cell under conditions effective to permit the cell to internalize the composition.

As used herein, the following terms shall have the indicated meanings.

The term "KD1" refers to Kunitz domain 1.

The term "NLS" refers to a nuclear localization signal. A NLS can often include one or more sequences of positively charged lysine or arginine residues. NLS sequences can be monopartite or bipartite. Bipartite NLS sequences often include two clusters of positively-charged amino acids that are separated by a spacer, which often includes about 10 amino acids.

The term "TFPI-2" refers to tissue factor pathway inhibitor-2.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, unless otherwise indicated, the recitations of numerical ranges by endpoints include all numbers subsumed within that range (e.g., 1 to 5 includes 1, 1.5, 2, 2.75, 3, 3.80, 4, 5, etc.).

The present invention provides an isolated polypeptide comprising a membrane transduction peptide of human tissue factor pathway inhibitor-2 (TFPI-2). As used herein, "polypeptide" refers to a polymer of amino acids linked by peptide bonds. Thus, for example, the terms "peptide," "oligopeptide," and "protein" are included within the definition of polypeptide and may be used interchangeably. The term "polypeptide" also refers to amino acid polymers having one or more post-translational modifications such as, for example, glycosylations, acetylations, phosphorylations, and the like. The term polypeptide does not connote a specific length of a polymer of amino acids. A polypeptide may be isolatable directly from a natural source, or can be prepared with the aid of recombinant, enzymatic, or chemical techniques. In the case of a polypeptide that is naturally occurring, such a polypeptide is typically isolated. An "isolated" polypeptide is one that has been removed from its natural environment. For instance, an isolated polypeptide is a polypeptide that has been removed from the cytoplasm or from the membrane of a cell, and many of the polypeptides, nucleic acids, and other cellular material of its natural environment are no longer present. Polypeptides that are produced outside the organism in which they naturally occur, e.g., through chemical or recombinant means, are considered to be isolated by definition, since they were never present in a natural environment.

In some embodiments, a membrane transduction peptide includes at least five contiguous amino acids from amino acids 187-213 of SEQ ID NO:1 such as, for example, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, or all 27 amino acids from amino acids 187-213 of SEQ ID NO:1. Unless otherwise specifically indicated, reference to at least a specified number of contiguous amino acids from a particular portion of SEQ ID NO:1 can include amino acid sequences that include any integer of contiguous amino acids of the recited portion of SEQ ID NO:1 equal to or greater than the specified number of contiguous amino acids, including the entire amino acid sequence of the recited portion of SEQ ID NO:1. Thus, for example, reference to at least five contiguous amino acids from amino acids 191-198 of SEQ ID NO1 can refer to at least five, at least six, at least seven, or all eight contiguous amino acids from amino acids 191-198 of SEQ ID NO:1.

In some embodiments, a membrane transduction peptide of human TFPI-2 includes at least five contiguous amino acids from amino acids 191-211 of SEQ ID NO:1. In other embodiments, a membrane transduction peptide of human TFPI-2 includes at least five contiguous amino acids from amino acids 187-213 of SEQ ID NO:1. For example, the membrane transduction peptide can include amino acids 191-211 of SEQ ID NO:1, amino acids 190-211 of SEQ ID NO:1, amino acids 189-211 of SEQ ID NO:1, amino acids 188-211 of SEQ ID NO:1, amino acids 187-211 of SEQ ID NO:1, amino acids 191-212 of SEQ ID NO:1, amino acids 190-212 of SEQ ID NO:1, amino acids 189-212 of SEQ ID NO:1, amino acids 188-212 of SEQ ID NO:1, amino acids 187-212 of SEQ ID NO:1, amino acids 191-213 of SEQ ID NO:1, amino acids 190-213 of SEQ ID NO:1, amino acids 189-213 of SEQ ID NO:1, amino acids 188-213 of SEQ ID NO:1, or amino acids 187-213 of SEQ ID NO:1.

Figure 4A:
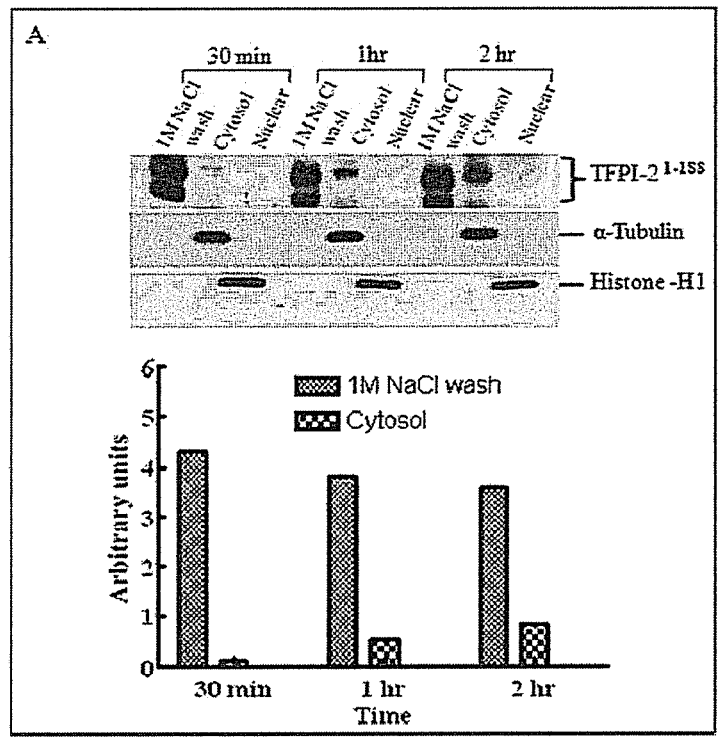
FIG. 4. Internalization of recombinant R24K KD1-CT and TFPI-$2^{1-188}$ and localization of overexpressing TFPI-$2^{1-188}$ in HT-1080 cells by immunoblotting and immunocytochemistry. (A) Cells grown in six-well plates were treated with 1 μM TFPI-$2^{1-188}$ and incubated at 37° C. for the indicated times. (B) Cells were treated with either 1 μM R24K KD1 or 1 μM R24K KD1-CT and incubated at 37° C. for five minutes. Cells from both (A) and (B) experiments were harvested for fractionation to detect the offered protein. The fractions were probed with anti-TFPI-2 antibody. The purity of cytosolic and nuclear fractions was verified using anti-α-tubulin and anti-histone-H1 antibodies, respectively. For immunoblot analysis, the intensity of blot bands were assessed by densitometric semi-quantitation and depicted by a bar diagram (lower panels). (C) Total cell lysate and cell fractions from stably transfected cells were prepared and probed with anti-TFPI-2 antibody. For immunoblot analysis, the intensity of blot bands were assessed by densitometric semi-quantitation and depicted by a bar diagram (lower panel). (D) The control and TFPI-$2^{1-188}$ overexpressing cells were grown on two-chamber culture slides and immunostained with murine monoclonal antibody SK-9 followed by Alexa Fluor 555-conjugated goat anti-mouse IgG as the secondary antibody. The nucleus is counterstained using DAPI in mounting media: (a) HT-1080 cells, and (b) HT-1080 cells overexpressing TFPI-$2^{1-188}$.
Figure 4B:
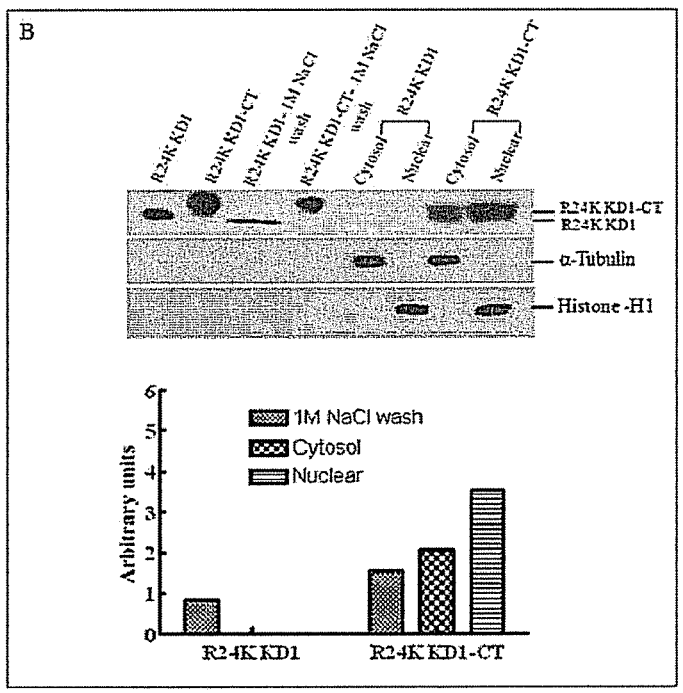

A membrane transduction peptide of human TFPI-2 can facilitate the transduction of a material (e.g., a fusion polypeptide and/or other material described in more detail below) containing the membrane transduction polypeptide across the plasma membrane of target cells. FIG. 4B shows that a chimeric polypeptide that includes a modified TFPI-2 KD1 domain and amino acids 187-213 of SEQ ID NO:1 (R24K KD1-CT, SEQ ID NO:2) is internalized to both the cytosol and nuclear fractions of HT-1080 cells after being incubated with the cells for five minutes at 37° C. In contrast, a polypeptide that includes only the modified TFPI-2 KD1 domain (R24K KD1) is not internalized to either the cytosol or nucleus of HT-1080 cells after being incubated with the cells for five minutes at 37° C. (FIG. 4B). Similarly, a polypeptide lacking amino acids 189-213 of SEQ ID NO:1 (TFPI-2$^{1-188}$) is not internalized as readily to either the cytosol or nucleus of HT-1080 cells after being incubated with the cells for 30 minutes at 37° C. (FIG. 4A).

Thus, in one aspect, a polypeptide of the invention can include any portion of human TFPI-2 that includes a membrane transduction peptide, with the proviso that the polypeptide is not the complete human TFPI-2 polypeptide (SEQ ID NO:1). A polypeptide that includes a membrane transduction peptide can facilitate cellular internalization of a material—e.g., a heterologous peptide domain, but other materials are expressly contemplated and are described in more detail below—to which the membrane transduction peptide of human TFPI-2 is coupled.

In addition to facilitating transduction across the plasma membrane, the carboxy-terminal tail of TFPI-2 may promote translocating TFPI-2 to the cell nucleus. Thus, certain membrane transduction peptides can promote translocating a material that is coupled to the membrane transduction peptide to the cell nucleus. As a consequence, certain membrane transduction peptides can promote localized delivery of a material to the nucleus of a target cell.

The carboxy-terminal of TFPI-2 includes a consensus bipartite nuclear localization signal (NLS) (KKKKKMPKL-RFASRIRKIRKK, amino acids 191-211 of SEQ ID NO:1). Bipartite NLS sequences have been experimentally demonstrated in 31 other nuclear-associated proteins, but the bipartite sequence described herein is unique. Thus, in certain embodiments, a membrane transduction peptide of TFPI-2 can include one or more arginine- and/or lysine-rich sequences of the carboxy terminal of TFPI-2. For example, a membrane transduction peptide of human TFPI-2 can include the five consecutive lysine residues at amino acids 191-195 of SEQ ID NO:1. Alternatively, or in addition, the membrane transduction peptide of human TFPI-2 can include at least five contiguous amino acids from the R/K-rich amino acids 204-211 of SEQ ID NO:1 such as, for example, at least five contiguous amino acids from amino acids 206-211 of SEQ ID NO:1. While the NLS sequence of TFPI-2 is bipartite, this appears to be a redundancy mechanism; translocation into the nucleus may be promoted by at least five contiguous amino acids from one (e.g., amino acids 191-195 of SEQ ID NO:1), the other (e.g., amino acids 204-211 of SEQ ID NO:1), or both of the lysine-rich or R/K-rich amino acid sequences.

In certain embodiments in which the membrane transduction peptide includes one or more arginine- and/or lysine-rich sequences, the membrane transduction peptide includes no more than 11 consecutive lysine residues or 11 consecutive arginine residues such as, for example, no more than 10 consecutive lysine residues or 10 consecutive arginine residues, no more than nine consecutive lysine residues or nine consecutive arginine residues, no more than eight consecutive lysine residues or eight consecutive arginine residues, no more than seven consecutive lysine residues or seven consecutive arginine residues, no more than six consecutive lysine residues or six consecutive arginine residues, or no more than five consecutive lysine residues or five consecutive arginine residues.

In some embodiments, therefore, the membrane transduction peptide can include amino acids 191-195 of SEQ ID NO:1 such as, for example, amino acids 186-195 of SEQ ID NO:1, amino acids 186-198 of SEQ ID NO:1, amino acids 187-195 of SEQ ID NO:1, amino acids 187-198 of SEQ ID NO:1, amino acids 191-198 of SEQ ID NO:1, or any combination thereof. In other embodiments, the membrane transduction peptide can include at least five contiguous amino acids from amino acids 206-211 of SEQ ID NO:1 such as, for example, amino acids 206-210 of SEQ ID NO:1, amino acids 206-211 of SEQ ID NO:1, amino acids 207-211 of SEQ ID NO:1, amino acids 198-211 of SEQ ID NO:1, amino acids 198-213 of SEQ ID NO:1, amino acids 206-213 of SEQ ID NO:1, or any combination thereof. In other embodiments, the membrane transduction peptide can include at least five contiguous amino acids from amino acids 204-211 of SEQ ID NO:1 such as, for example, amino acids 204-208 of SEQ ID NO:1, amino acids 204-210 of SEQ ID NO:1, amino acids 204-211 of SEQ ID NO:1, or any combination thereof.

Also, a membrane transduction peptide can include any combination of two or more amino acid sequences chosen from amino acids 191-195 of SEQ ID NO:1, at least five contiguous amino acids from amino acids 206-211 of SEQ ID NO:1, and/or at least five contiguous amino acids from amino acids 204-211 of SEQ ID NO:1.

Thus, the carboxy-terminal tail of TFPI-2—and, by extension, a membrane transduction peptide contained therein—may be bifunctional, containing a transduction domain that promotes efficient and rapid penetration of the domain (and any material coupled to the membrane transduction domain) through the plasma membrane of a target cell and an NLS sequence that promotes translocation of the membrane transduction domain (and any material coupled to the membrane transduction domain) into the nucleus of the target cell. Because a membrane transduction peptide may be bifunctional, a membrane transduction peptide to promote localization to the nucleus of a target cell need not include a nuclear transduction domain (e.g., an NLS sequence) separate from one that exists as part of a plasma membrane transduction domain.

In some embodiments, a membrane transduction peptide can include a peptide that is structurally similar to a stated reference amino acid sequence. As used herein, a peptide is "structurally similar" to a reference amino acid sequence if the amino acid sequence of the peptide possesses a specified amount of identity compared to the reference amino acid sequence. Structural similarity of two peptides can be determined by aligning the residues of the two amino acid sequences (e.g., a candidate peptide amino acid sequence and amino acids 191-211 of SEQ ID NO:1) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate peptide is the peptide being compared to the reference amino acid sequence (e.g., amino acids 191-211 of SEQ ID NO:1). A candidate peptide can be isolated, for example, from a natural source, or can be produced using recombinant techniques, or chemically or enzymatically synthesized.

A pair-wise comparison analysis of amino acid sequences can be carried out using the BESTFIT algorithm in the GCG package (version 10.2, Madison Wis.). Alternatively, peptides may be compared using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a membrane transduction peptide may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a peptide containing deletions or additions of one or more contiguous or noncontiguous amino acids that do not eliminate a functional activity of the peptide are also contemplated.

A membrane transduction peptide can include a peptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to a reference amino acid sequence.

For example, a membrane transduction peptide based on either of the lysine-rich or R/K-rich amino acid sequences within amino acids 187-213 of SEQ ID NO:1 (e.g., amino acids 191-195, amino acids 204-211, or amino acids 206-211) can include one or more arginine for lysine substitutions and/or one or more lysine for arginine substitutions. Additionally, such a membrane transduction peptide can include one or more substitutions of a lysine or arginine for an uncharged amino acid (e.g., alanine, leucine, isoleucine, etc.) and/or an addition of one or more amino acid residues (e.g., a positively charged amino acid residue such as arginine, lysine, or histidine). Of course, membrane transduction peptides containing other modifications of amino acids 191-195, amino acids 204-211, and/or amino acids 206-211 of SEQ ID NO:1 arte possible. Also, membrane transduction peptides based on other portions of amino acids 187-213 of SEQ ID NO:1 that include one or more additions, substitutions, or deletions compared to the reference amino acid sequence are possible as well.

In another aspect, an isolated polypeptide of the invention can include a membrane transduction domain that includes a membrane transduction peptide of human TFPI-2 and a heterologous polypeptide domain. As used herein, a "heterologous polypeptide domain" refers to one or more contiguous amino acids from a peptide, polypeptide, or protein that is not human TFPI-2. Such an isolated polypeptide may be a fusion or chimeric polypeptide and may be prepared using recombinant, synthetic, or chemical methods well known to those skilled in the art. Such a polypeptide may be prepared for, for example, administering to target cells in order to obtain cells in which the heterologous polypeptide domain is internalized into the target cells.

The membrane transduction peptide of human TFPI-2 included in the membrane transduction domain may be any of the membrane transduction peptides previously described, including combinations of membrane transduction peptides, and including particular membrane transduction peptides expressly identified herein.

The isolated polypeptide may be prepared using any suitable method such as, for example, recombinant, synthetic, and/or chemical methods. For example, the polypeptide may be prepared by expressing in an appropriate host cell a polynucleotide that encodes a polypeptide that includes both the membrane transduction domain and a heterologous polypeptide domain (e.g., a fusion or chimeric polypeptide).

Also included in the invention is a polynucleotide including a nucleotide sequence that encodes a polypeptide of the invention such as, for example, a membrane transduction peptide of human TFPI-2, a fusion protein including a membrane transduction domain and a heterologous polypeptide domain, etc. The term "polynucleotide" refers broadly to a polymer of two or more nucleotides covalently linked in a 5' to 3' orientation. The terms "nucleic acid," "nucleic acid sequence," and "oligonucleotide" are included within the definition of polynucleotide and these terms may be used interchangeably. It should be understood that these terms do not connote a specific length of a polymer of nucleotides, nor are they intended to imply or distinguish whether the polynucleotide is produced using recombinant techniques, chemical or enzymatic synthesis, or is naturally occurring. The polynucleotides of the invention can be DNA, RNA, or a combination thereof, and can include any combination of naturally occurring, chemically modified, or enzymatically modified nucleotides.

Polynucleotides can be single-stranded or double-stranded. In the case of double-stranded polynucleotides, the sequence of the second, complementary strand is dictated by the sequence of the first strand. The term "polynucleotide" is therefore to be broadly interpreted as encompassing a single stranded nucleic acid polymer, its complement, and the duplex formed by complementary strands. "Complementarity" of polynucleotides refers to the ability of two single-stranded polynucleotides to base pair with each other, in which an adenine on one polynucleotide will base pair with a thymidine (or uracil, in the case of RNA) on the other, and a cytidine on one polynucleotide will base pair with a guanine on the other. Two polynucleotides are complementary to each other when a nucleotide sequence in one polynucleotide can base pair with a nucleotide sequence in a second polynucleotide. For instance, 5'-ATGC and 5'-GCAT are fully complementary, as are 5'-GCTA and 5'-TAGC.

Polynucleotides of the invention include polynucleotides having a nucleotide sequence that is "substantially complementary" to (a) a nucleotide sequence that encodes a polypeptide according to the invention, or (b) the complement of such nucleotide sequence. "Substantially complementary" polynucleotides can include at least one base pair mismatch, such that at least one nucleotide present on a second polynucleotide, however the two polynucleotides will still have the capacity to hybridize. For instance, the middle nucleotide of each of the two DNA molecules 5'-AGCAAATAT and 5'-ATATATGCT will not base pair, but these two polynucleotides are nonetheless substantially complementary as defined herein. Two polynucleotides are substantially complementary if they hybridize under hybridization conditions exemplified by 2X SSC (SSC: 150 mM NaCl, 15 mM trisodium citrate, pH 7.6) at 55° C. Substantially complementary polynucleotides for purposes of the present invention preferably share at least one region of at least 15 nucleotides in length which shared region has at least 60% nucleotide identity, preferably at least 80% nucleotide identity, more preferably at least 90% nucleotide identity and most preferably at least 95% nucleotide identity. Particularly preferred substantially complementary polynucleotides share a plurality of such regions.

Nucleotide sequences are preferably compared using the Blastn program, version 2.2.10, of the BLAST 2 search algorithm, also as described by Tatusova et al. (FEMS Microbiol. Lett, 174, 247-250 (1999)), and available on the National Center for Biotechnology Information website, under BLAST in the Molecular Database section. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. Locations and levels of nucleotide sequence identity between two nucleotide sequences can also be readily determined using CLUSTALW multiple sequence alignment software (J. Thompson et al., Nucl. Acids Res., 22:4673-4680 (1994)), available at the European Bioinformatics Institute website in the "Toolbox" section as the ClustalW program.

A polynucleotide that encodes an isolated polypeptide described herein is not limited to a polynucleotide that contains all or a portion of naturally occurring genomic or cDNA nucleotide sequence, but also includes the class of polynucleotides that encode such polypeptides as a result of the degeneracy of the genetic code. The class of nucleotide sequences that encode a selected polypeptide sequence is large but finite, and the nucleotide sequence of each member of the class can be readily determined by one skilled in the art by reference to the standard genetic code, wherein different nucleotide triplets (codons) are known to encode the same amino acid. In another aspect, the present invention provides a method of delivering a material to a target cell. Generally, the method includes providing a composition that includes the material coupled to a membrane transduction domain—which includes a membrane transduction peptide of human TFPI-2 as described herein—and contacting the composition with the target cell under conditions effective to permit the target cell to internalize the composition.

In the method described herein, the membrane transduction domain and membrane transduction peptide can be any of the membrane transduction domains and membrane transduction peptides, respectively, already described herein, including combinations thereof.

The material may be any material that can be internalized by a target cell when coupled to a membrane transduction domain. Exemplary materials include, but are not limited to biological materials such as, for example, a polypeptide, a nucleic acid, or a liposome. In certain embodiments, the material can include an active agent such as, for example, a drug or prodrug. As used herein, a prodrug is a pharmacological material (e.g., a drug) that is administered in an inactive (or significantly less active) form. Once administered, the prodrug can be metabolized in vivo into an active form of the pharmacological material—e.g., an active form of a drug. In other embodiments, the active agent can include a nucleic acid or a fluorophore. Thus, in some cases, a material (e.g., a drug or prodrug) may be intended to alter the physiology of the target cell. In other cases, a material (e.g., fluorophore) may be intended to help identify the cell. Consequently, the method described herein is in no way limited by the particular function of the material internalized by the target cell as a consequence of being coupled to a membrane transduction domain.

The membrane transduction domain may be coupled to the material in any manner that allows the coupled composition to be internalized by a target cell. In some embodiments, the membrane transduction domain and the material may be directly covalently bound. For example, the composition may be a fusion polypeptide that includes a membrane transduction domain covalently coupled by a peptide bond to a material that includes a functional domain of a polypeptide for which internalization by the target cell is desired. In other cases, the membrane transduction domain and the material may be coupled by crosslinking or by affinity coupling (e.g., avidin-biotin affinity). Thus, in some embodiments, the composition can include a linking component between the membrane transduction domain and the material. The linking component can include, for example, an avidin-biotin complex, crosslinking, or a nanoparticle (e.g., to which each of the membrane transduction domain and the material is coupled). Methods of crosslinking, forming avidin-biotin complexes, and forming nanoparticle complexes using biological materials while maintaining biological, physical, chemical, and/or pharmacological activity of the components being coupled in these ways are routine and well known to those skilled in the art.

The membrane transduction domain and the material may be coupled by any method suitable for the particular manner in which the components are coupled. The components may be coupled using, for example, recombinant, synthetic, and/or chemical methods. For example, in embodiments in which the material is a peptide, the composition made be prepared by expressing in an appropriate host cell a polynucleotide that encodes a polypeptide that includes both the membrane transduction domain and the material (e.g., a fusion or chimeric polypeptide). In other cases, the membrane transduction domain may be coupled to a material that chemically or enzymatically dissociates from the membrane transduction domain following internalization into the cell.

The target cell can be any target cell for which internalization of a particular material is desired. For example, a suitable target cell may be a cell (e.g., a tumor cell) that is the target of the material to be internalized (e.g., an anti-tumor active agent). In other examples, the target cells may be cells involved in maintaining the blood brain barrier in vivo. In still other examples, the target cells may be involved in differentiating human embryonal stem cells in vitro. In some cases, the target cell may be in a living organism such as, for example, in a tissue or organ of the organism.

In some embodiments, the method includes contacting the composition with the target cell under conditions effective to permit the target cell to internalize the composition. In some cases, internalizing the composition includes internalizing the composition to at least a portion of the target cell's cytoplasm. In other cases, internalizing the composition includes internalizing the composition to at least a portion of the target cell's nucleus. In some embodiments, conditions effective to permit a target cell to internalize the composition include in vivo conditions such as, for example, physiological temperature and/or pH.

In embodiments in which it is desired to localize the material to the nucleus of the target cell, the membrane transduction peptide can include, for example, a bifunctional amino acid sequence that promotes both transduction of the material across the plasma membrane of the target cell and translocation of the material, once inside the target cell, to the nucleus. In certain embodiments, however, the membrane transduction peptide need not be bifunctional. Thus, in certain embodiments, the membrane transduction peptide may promote transduction of the material across the plasma membrane of the target cell and localization of the material to the target cell nucleus may be accomplished by any other suitable method known to those skilled in the art. Alternatively, transduction of the material across the plasma membrane of the target cell may be accomplished by any suitable method known to those skilled in the art and translocation of the material into the target cell nucleus may be promoted by the membrane transduction peptide.

In the course of previous studies, we observed that a portion of the TFPI-2 offered to the HT-1080 fibrosarcoma cells was internalized, as the cell lysate contained significant amounts of immunoreactive TFPI-2 following a 48-hour incubation. The present study was initiated to further investigate the intracellular distribution of offered TFPI-2 in cell lines that do not secrete this protein, and compare these patterns with cells that either constitutively synthesize TFPI-2 or stably transfected to overexpress this protein. Using immunoblotting and immunocytochemistry approaches, we demonstrate that offered TFPI-2 is rapidly internalized in cells that do not constitutively synthesize this protein and is translocated to the nucleus. Nuclear localization of TFPI-2 was also observed in cells that constitutively synthesize TFPI-2, as well as cells overexpressing this molecule. Further, the TFPI-2 carboxy-terminal tail contains a putative bipartite nuclear localization signal (NLS), and truncated TFPI-2 lacking the carboxy-terminal tail was not detected in the nucleus. Moreover, the carboxy-terminal tail of TFPI-2 also appears to play a role in the transduction of TFPI-2 through the cell membrane. Thus, TFPI-2 may regulate one or more serine proteinases involved in proteolytic degradation of nuclear components.

Figure 1B:
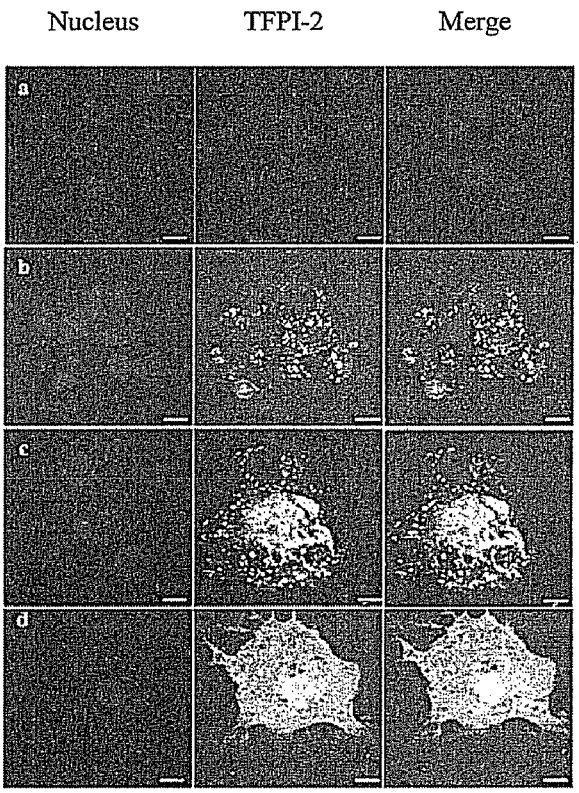
Figure 1C:
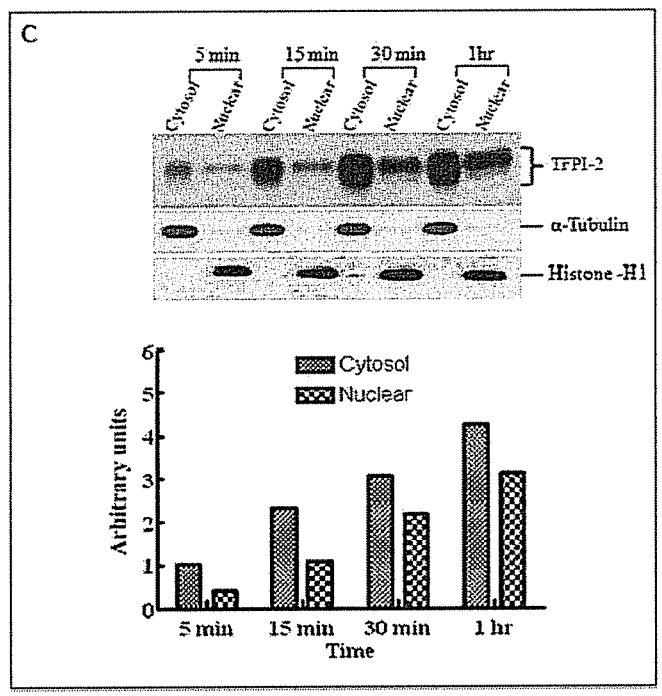
Figure 1D:
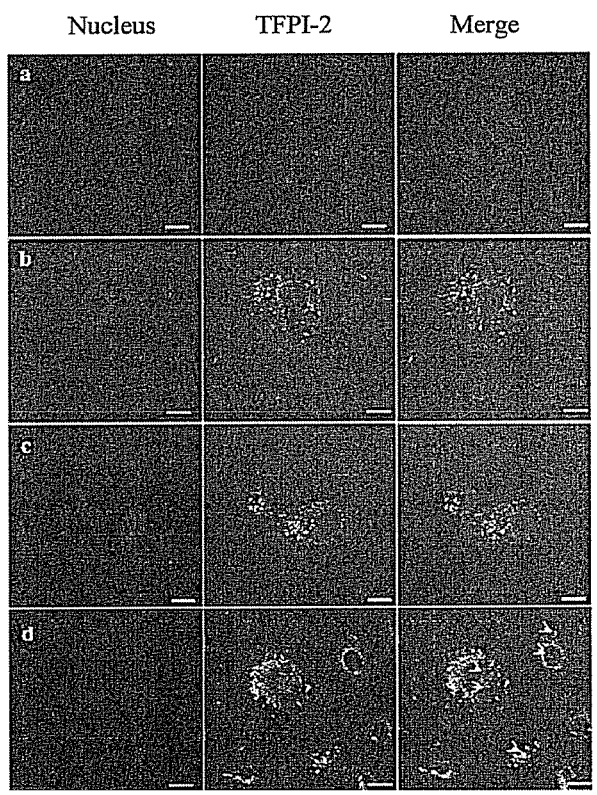

Previously, exogenous TFPI-2 has been demonstrated to induce caspase-mediated apoptosis in several human tumor cell lines (Kempaiah and Kisiel, Apoptosis, 2008;13:702-715). Moreover, recombinant TFPI-2 offered to a human fibrosarcoma cell line, HT-1080, was internalized by these cells but was not degraded intracellularly (Kempaiah and Kisiel, Apoptosis, 2008;13:702-715). To assess the functional significance of TFPI-2 internalization by these cells, we initially incubated HT-1080 cells with 1 μM TFPI-2 for various time periods (24-72 hours) and subsequently assessed the intracellular distribution of the internalized TFPI-2. Using immunoblotting techniques, we observed that TFPI-2 was internalized and distributed in both the cytosolic and the nuclear fractions (FIG. 1). Maximal cytosolic and nuclear localization of TFPI-2 by these cells occurred at 48 hours, and diminished after 72 hours of incubation. To investigate the rate at which TFPI-2 was internalized and translocated to the nucleus, we offered TFPI-2 (1 μM) to the HT-1080 cells and temporally assessed TFPI-2 intracellular distribution within the first 15 minutes of offering. TFPI-2 is rapidly internalized by these cells and translocated to the nucleus within minutes of offering (FIG. 1A). The integrity of each cellular fraction was verified by separate immunoblotting experiments of these fractions using anti-α-tubulin IgG and anti-histone H1 IgG as cytosolic and nuclear markers, respectively (FIG. 1A). Consistent with the immunoblotting results, confocal microscopy using Alexa Fluor 488-conjugated TFPI-2 revealed cytosolic and nuclear localization of TFPI-2 following a two-hour incubation with the HT-1080 cells at 37° C., whereas vehicle-treated cells revealed no fluorescence under identical conditions (FIG. 1B). Internalization and translocation of TFPI-2 to the nucleus was temperature-dependent, as the amount of TFPI-2 localized in the nucleus in 60 minutes at 4° C. was roughly equivalent to that observed in five minutes at 37° C. (FIG. 1C). In addition, confocal microscopy of Alexa Fluor 488-conjugated TFPI-2 incubated for five minutes, 10 minutes, and two hours at 4° C. revealed a limited punctate distribution of TFPI-2 in the cytosol at five minutes and 10 minutes. At the two hour time point at 4° C., significant cytosolic and nuclear-associated TFPI-2 was also observed (FIG. 1D). In contrast, uniform distribution of TFPI-2 was observed in cells at 37° C. at the two hour time point (FIG. 1B). In contrast to the complete TFPI-2 molecule, R24K KD1 and R24Q KD1, each at 1 μM concentrations, failed to be internalized by HT-1080 cells following a 48-hour incubation at 37° C. This result suggests that either the intact molecule or TFPI-2 domains other than the KD1 domain were required for cell binding and/or internalization.

Figure 2A:
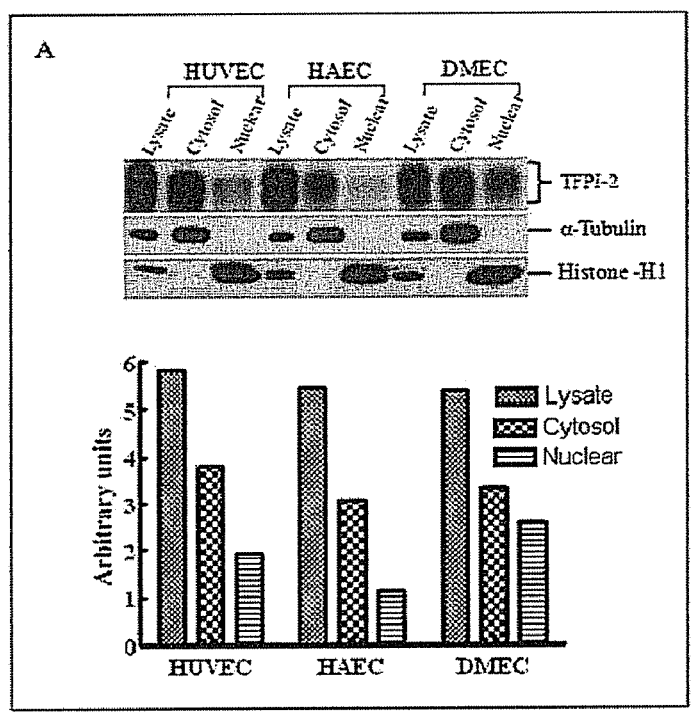
FIG. 2A-2B. Intracellular distribution of TFPI-2 in endothelial cells assessed by immunoblotting and immunocytochemistry. To investigate the intracellular distribution of endogenously expressed TFPI-2 protein in endothelial cells, HUVEC, HAEC and DMEC cells were cultured under standard growth conditions. (A) For immunoblotting, lysate and cell fractions from all cells were prepared and probed with anti-TFPI-2 IgG. The purity of cytosolic and nuclear fractions was verified using anti-α-tubulin and anti-histone-H1antibodies, respectively. For immunoblot analysis, the intensity of blot bands were assessed by densitometric semi-quantitation and depicted by a bar diagram (lower panel). (B) DMEC cells were grown on two-chamber culture slides and immunostained with murine monoclonal antibody SK-9 and Alexa Fluor-555-conjugated goat anti-mouse IgG as the secondary antibody. The nucleus is counterstained using DAPI in mounting media: (a) vehicle plus Alexa Fluor-555-conjugated goat anti-mouse IgG, and (b) SK-9 antibody and Alexa Fluor-555-conjugate goat anti-mouse IgG.
Figure 2B:
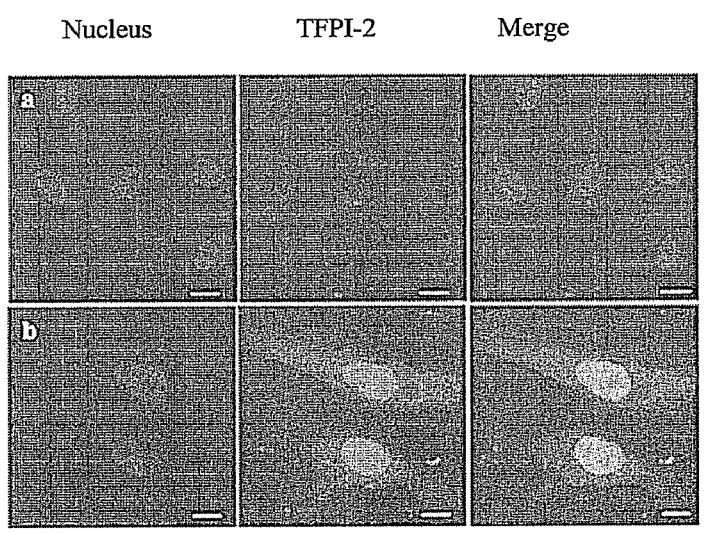
Figure 3A:
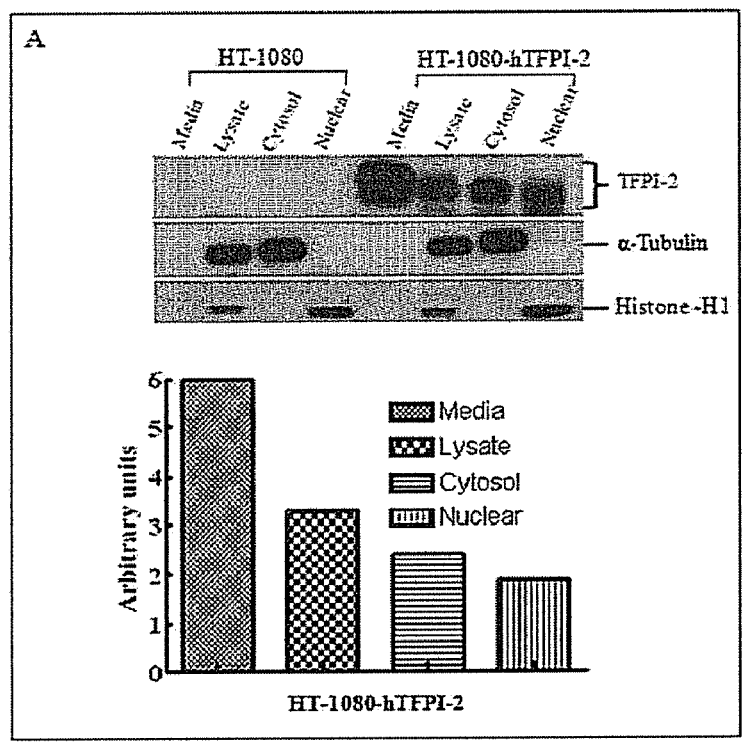
FIG. 3A-3B. Analyses of TFPI-2 localization in untransfected and stably-transfected HT-1080 cells by immunoblotting and immunocytochemistry. Wild-type HT-1080and HT-1080 cells stably-transfected with hTFPI-2 cDNA were cultured under standard growth conditions. (A) For immunoblotting, total lysate and cell fractions were prepared and probed with anti-TFPI-2 antibody. The purity of cytosolic and nuclear fractions was verified using anti-α-tubulin and anti-histone-H1 antibodies, respectively. For immunoblot analysis, the intensity of blot bands were assessed by densitometric semi-quantitation and depicted by a bar diagram (lower panel). (B) For immunocytochemistry, cells were grown on two-chamber culture slides and incubated with murine monoclonal antibody SK-9 followed by Alexa Fluor-555-conjugated goat anti-mouse IgG as the secondary antibody. The nucleus is counterstained using DAPI in mounting media: (a) HT-1080 cells, and (b) HT-1080 cells overexpressing TFPI-2.
Figure 3B:
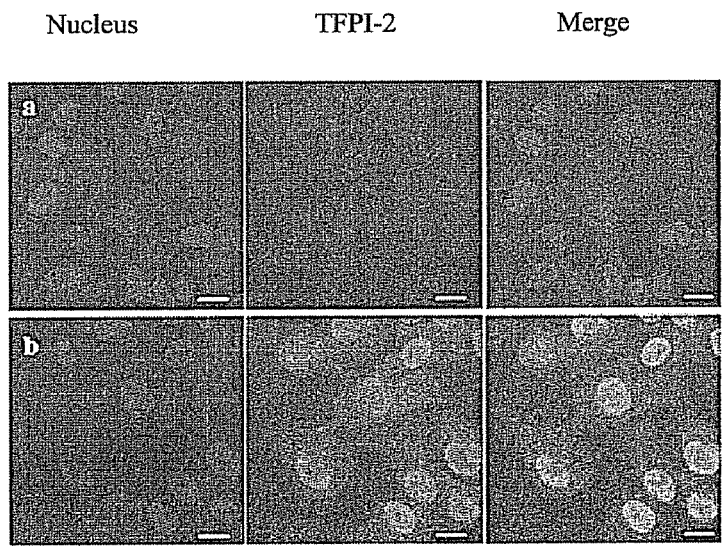

Having demonstrated that exogenous TFPI-2 was internalized by HT-1080 cells that do not synthesize TFPI-2, we next investigated whether TFPI-2 was nuclear-associated in cells that either constitutively synthesize this protein or cells stably-transfected with TFPI-2 cDNA to express this protein. Our initial studies focused on three human endothelial cells lines derived from umbilical vein (HUVEC), aorta (HAEC) and dermal microvascular (DMEC), all known to express varying amounts of TFPI-2 (Iino et al., *Arterioscler. Thromb. Vasc. Biol.*, 1998;18:40-46). The results of immunoblotting experiments of endothelial cell fractions clearly demonstrate cytosolic and nuclear localization of TFPI-2 by these cells (FIG. 2A). Immunocytochemistry studies, using a TFPI-2-specific murine monoclonal antibody (SK-9) and Alexa Fluor 555-conjugated goat anti-mouse IgG secondary antibody confirmed the cytosolic and nuclear localization of TFPI-2 in DMECs (FIG. 2B), whereas cells treated exclusively with secondary antibody exhibited no fluorescence, attesting to the specificity of SK-9. Immunoblotting and immunocytochemistry of HT-1080 cells overexpressing TFPI-2 also demonstrated cytosolic and nuclear localization of TFPI-2 in comparison to untransfected cells (FIG. 3). In addition, essentially identical results were obtained with HEK 293 cells overexpressing TFPI-2.

Inasmuch as several internalized or cytosolic proteins are transported to the nucleus by importins that recognize and bind to NLS sequences in proteins (Planque, N. *Cell Communication and Signaling*, 2006;4:7), we subjected the TFPI-2 sequence to an in silico analysis using PredictNLS Imput program (accessible online at the website maintained by Burkhard Rost, Columbia University, Department of Biochemistry and Molecular Biophysics and the Center for Computational Biology) to determine if it contained a consensus NLS site. The analysis identified a putative bipartite NLS sequence (KKKKKMPKLRFASRIRKIRKK, amino acids 191-211 of SEQ ID NO:1) at the carboxy-terminal tail of TFPI-2. As discussed above, while bipartite NLS sequences have been experimentally demonstrated in other nuclear-associated proteins, the bipartite sequence NLS sequence of human TFPI-2 described herein is unique.

Figure 4C:
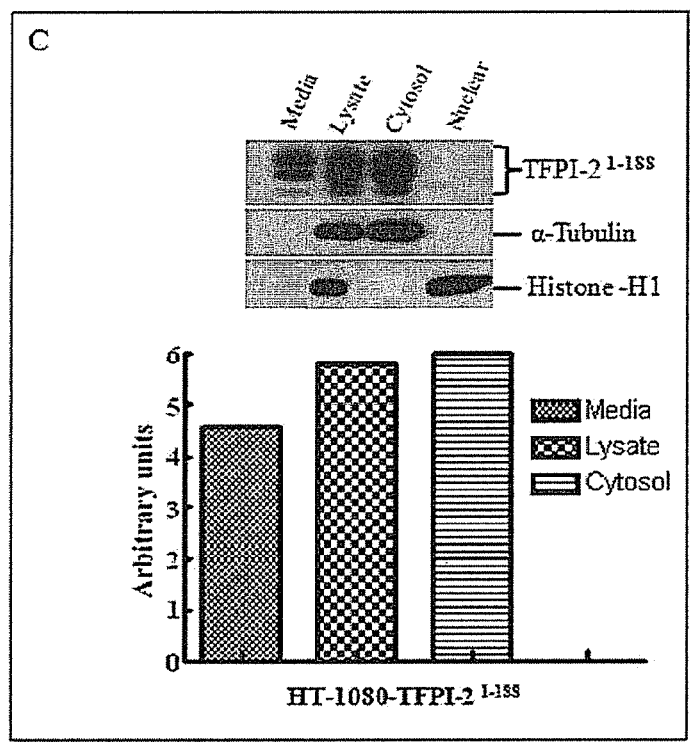
Figure 4D:
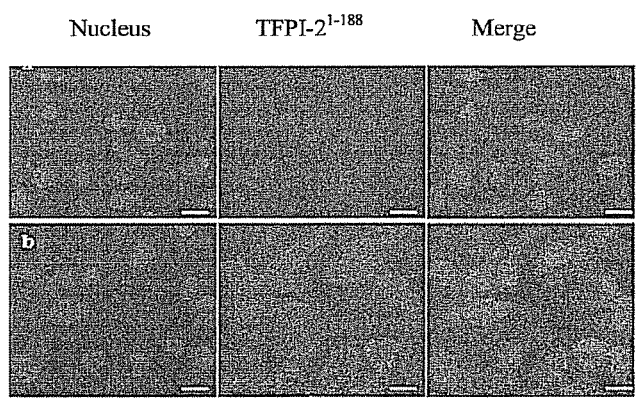

In order to determine whether the NLS sequence is involved in the translocation of TFPI-2 to the nucleus, we expressed and purified a TFPI-2 construct (TFPI-$2^{1-188}$) devoid of the carboxy-terminal tail, as well as a chimera of the first Kunitz-type domain and the carboxy-terminal tail (R24K KD1-CT). We then offered these purified peptides to HT-1080 cells and monitored their intracellular trafficking by immunoblot analyses. TFPI-$2^{1-188}$ was slowly internalized, but failed to be transported to the nucleus (FIG. 4A). While the R24K KD1 failed to enter the cells, the R24K KD1-CT chimera was rapidly internalized and translocated to the nucleus by HT-1080 cells within five minutes (FIG. 4B). In addition, HT-1080 cells stably transfected with an expression vector bearing the TFPI-$2^{1-188}$ cDNA also failed to demonstrate nuclear localization (FIG. 4C). Immunocytochemical analyses confirmed that TFPI-$2^{1-188}$ was confined to the cytoplasm in the HT-1080 cells overexpressing this protein (FIG. 4D).

Having demonstrated that TFPI-2 contains a putative bipartite NLS sequence that permits translocation of polypeptides to the nucleus, we next performed co-immunoprecipitation studies to determine whether TFPI-2 was forming complexes with importin-α, a cytosolic protein that binds to NLS-bearing proteins. Using either an anti-TFPI-2 monoclonal antibody (SK-9) or an anti-importin-α monoclonal antibody, each coupled to an insoluble resin, complexes of TFPI-2 and importin-α were immunoprecipitated by each antibody from the cell lysates of either TFPI-2-treated HT-1080 cells or HT-1080 cells overexpressing TFPI-2 (FIG. 5). In contrast, wild-type, untransfected HT-1080 cell lysates immunoprecipitated with SK-9 failed to yield TFPI-2-importin-α complexes, while importin-α was readily immunoprecipitated from all cell lysates by the anti-importin-α antibody (FIG. 5). These results provide definitive evidence that TFPI-2 fauns cytosolic complexes with importin-α, which ultimately interacts with importin-β, the karyopherin that chaperones this ternary complex through the nuclear pore complex (Goldfarb et al. *Trends Cell Biol.*, 2004;14:505-514).

We previously reported that human TFPI-2, an ECM-associated Kunitz-type serine proteinase inhibitor, induces caspase-mediated apoptosis in several human tumor cell lines when exogenously offered to these cells (Kempaiah and Kisiel, *Apoptosis,* 2008;13:702-715). In the course of those studies, we observed that TFPI-2 was internalized by the human fibrosarcoma cell line HT-1080, which does not constitutively synthesize this protein (Kempaiah and Kisiel, *Apoptosis,* 2008;13:702-715). Using immunoblotting and immunocytochemistry approaches, we now report that TFPI-2 is rapidly internalized by HT-1080 cells and efficiently translocated to the nucleus. A bipartite NLS sequence located at the carboxy-terminal tail of TFPI-2 facilitates translocation of polypeptides bearing the NLS sequence—whether naturally or recombinantly—permits rapid internalization of TFPI-2 by these cells. In this regard, we observed that a mutant of the first Kunitz-type domain of TFPI-2 (R24K KD1) was not internalized by HT-1080 cells. However, a chimera of this domain and the carboxy-terminal tail, R24K KD1-CT, was rapidly internalized by these cells. As offered TFPI-2 and R24KD 1-CT were each internalized and translocated to the nucleus within minutes, the likelihood that these are internalized through some receptor-mediated endocytic process seems unlikely. This possible mode of cellular entry does not rule out additional, perhaps receptor-mediated, mechanisms for TFPI-2 internalization since the TFPI-2 construct lacking the carboxy-terminal tail was also internalized by these cells, albeit at a very slow rate in relation to the intact TFPI-2 molecule and the R24K KD1-CT chimera. Accordingly, the carboxy-terminal tail of TFPI-2, which contains a large number of arginine and lysine residues, appears to be responsible for efficient protein transduction through the plasma membrane, similar to that observed for the *Drosophila* Antennapedia homeoprotein (Derossi et al., *J. Biol. Chem.,* 1994;269: 10444-10450, Derossi et al., *J. Biol. Chem.;* 1996;271: 18188-18193), the HIV-1 TAT protein transduction domain (Frankel and Pabo, *Cell,* 1988;55:1189-1193), and 12-mers of polylysine and polyarginine (Mi et al., *Mol. Therapy,* 2000; 2:339-347).

In addition to facilitating cellular uptake, the carboxy-terminal tail of TFPI-2 also appears to be involved in translocating polypeptides containing the NLS sequence to the nucleus. Moreover, co-immunoprecipitation experiments revealed that TFPI-2 formed complexes with importin-α, a cytosolic protein that recognizes NLS-bearing proteins and, together with importin-β, shuttles these cargo proteins into the nucleus (Goldfarb et al. *Trends Cell Biol.,* 2004;14:505-514). Interestingly, in addition to TFPI-2-negative cells offered TFPI-2 protein, cells that either constitutively synthesize TFPI-2 or cells that overexpress this protein also contained TFPI-2 in their nuclei, suggesting that a portion of TFPI-2 is internalized by these cells post-secretion.

Thus, the carboxy-terminal tail of TFPI-2 may be bifunctional, containing a protein transduction domain that allows efficient and rapid penetration of the protein through the plasma membrane and an NLS sequence for translocation of the protein into the nucleus.

As TFPI-2 induces apoptosis in several tumor and endothelial cells, the question naturally arises as to whether internalization and nuclear translocation of TFPI-2 are associated with apoptosis induction in these cells. Inasmuch as R24K KD1, a more potent inducer of apoptosis than TFPI-2, failed to be internalized by HT-1080 cells following a 48-hour incubation, it would appear that internalization and apoptosis induction may be distinctly different and independent processes. Based on the available data, TFPI-2 localization into the nucleus appears to be a natural phenomenon seen in all cell types that synthesize and express this molecule.

In summary, the studies presented here reveal that human TFPI-2 is rapidly internalized by several different cell lines, and is translocated to the nuclei of these cells. Nuclear translocation of TFPI-2 required a putative NLS sequence in its carboxy-terminal tail, as well as complex formation with importin-α.

The present invention further provides compositions that include a polypeptide as described herein and a pharmaceutically acceptable carrier. "Pharmaceutically acceptable" refers to a diluent, carrier, excipient, salt, etc., that is compatible with the other ingredients of the composition, and not deleterious to the recipient thereof. Suitable excipients are, for example, water, saline, dextrose, glycerol, ethanol, or the like and combinations thereof. In addition, if desired, the pharmaceutical composition may contain minor amounts of auxiliary materials such as wetting or emulsifying agents, pH buffering agents and/or salts. Also, the pharmaceutical composition can include additional therapeutic agents.

The compositions of the present invention may be formulated in pharmaceutical preparations in a variety of fowls adapted to the chosen route of administration, including routes suitable for stimulating an immune response to an antigen. Thus, a composition of the present invention can be administered via known routes including, for example, orally or parenterally including intradermally, transcutaneously, subcutaneously, intramuscularly, intravenously, intraperitoneally, etc. and topically such as, for example, intranasally, intrapulmonarily, intramammarily, intravaginally, intrauterinely, intradenually, transcutaneously, rectally, etc. A composition can also be administered in a formulation that provides delayed release, timed release, or sustained release, using formulation well known to those skilled in the art. Methods of making and using such pharmaceutical compositions are also included in the invention.

The present invention is illustrated by the following examples. It is to be understood that the particular examples, materials, amounts, and procedures are to be interpreted broadly in accordance with the scope and spirit of the invention as set forth herein.

EXAMPLES

Materials and Methods

Cell Lines and Reagents

The human fibrosarcoma cell line (HT-1080) and primary embryonal kidney cell line (HEK 293), were obtained from American Type Culture Collection (Manassas, Va.). Human umbilical vein endothelial cells (HUVECs) were obtained from Cambrex (Walkersville, Md.). Human aorta endothelial cells (HAEC) and dermal capillary endothelial cells (DMEC), were obtained from Cell Systems (Kirkland, Wash.). Dulbecco's minimal essential medium (DMEM), penicillin, streptomycin, protease inhibitor cocktail, murine anti-human importin-α antibody, and murine anti-human α-tubulin antibody were purchased from Sigma-Aldrich (St. Louis, Mo.). Anti-Histone H1 antibody was obtained from Gene Tex (San Antonio, Tex.). Fetal bovine serum was obtained from Hyclone (Ogden, Utah). Nitrocellulose (NC) membranes, goat anti-rabbit IgG-HRP, goat anti-mouse IgG-HRP, and AffiGel 10 were obtained from Bio-Rad (Hercules, Calif.). Alexa Fluor 555-conjugated goat anti-mouse IgG was generously provided by Dr. Bridget Wilson. Alexa Fluor 488 protein labeling kit was purchased from Invitrogen (Carlsbad, Calif.). Mounting media with DAPI was from Vector Laboratories (Burlingame, Calif.). Chemiluminescent horseradish peroxidase (HRP) substrate was purchased from Millipore Corporation (Billerica, Mass.). Two-chamber culture slides were obtained from BD Bioscience (Bedford, Mass.). PROFOUND co-immunoprecipitation kit was purchased from Pierce (Rockford, Ill.). All other reagents were of the highest quality commercially available.

Cell Culture

HEK 293 and HT-1080 cell lines were maintained in Dulbecco's minimal essential medium (DMEM), supplemented with heat-inactivated 10% fetal bovine serum and penicillin-streptomycin. The cells were cultured at 37° C. in a humidified atmosphere containing 6% $CO_2$. Similarly, endothelial cells were maintained in medium 199 supplemented with 20% fetal bovine serum, 100 μg/ml heparin, 100 μg/ml endothelial cell growth supplement (ECGS) and penicillin-streptomycin.

Construction of Plasmids and Recombinant Protein Preparation

A TFPI-2 construct lacking the carboxy-terminal tail (TFPI-$2^{1-188}$) was generated by PCR amplification using pcDNA3-TFPI-2 as the template (Chand et al., *Blood*, 2004; 103:1069-1077), and the resulting amplicon subcloned into the EcoRI site of the pcDNA3.0 expression vector. An R24K KD1-C-tail chimera (R24K KD1-CT, SEQ ID NO:2) was prepared by ligating a KD1 fragment and a carboxy-terminal tail fragment, each generated by PCR amplification. A polynucleotide encoding the KD1 fragment (amino acids 1-73 of SEQ ID NO:1) was amplified from pET-R24K KD1 (Schmidt et al., *J Biol. Chem.*, 2005;280:27832-27838) using primer sets containing NdeI and EcoR I restriction sites, while a polynucleotide encoding a carboxy-terminal tail fragment (amino acids 187-213 of SEQ ID NO:1) was derived from the pcDNA3-TFPI-2 (Chand et al., *Blood*, 2004;103:1069-1077) using a primer set containing EcoR1 and Xho I restriction sites. Following amplification, the PCR products were digested with EcoRI and ligated to generate R24K KD1-CT, which was subsequently inserted into the Nde I/Xho I site of the pET28a expression vector. The resulting R24K KD1-CT polypeptide (SEQ ID NO:2) contains a vector-specific Glu-Phe dipeptide at the site of the ligation (i.e., between the KD-1 fragment and the carboxy-terminal fragment).

HT-1080 and HEK 293 cell lines were stably transfected to overexpress either wild-type human TFPI-2 or a mutant TFPI-2 construct lacking the carboxy-terminal tail (TFPI-$2^{1-188}$), and were maintained as described (Chand et al., *Blood*, 2004;103:1069-1077, Du et al., *Arch. Biochem. Biophys.*, 2003;417:96-104). An anti-human TFPI-2 murine monoclonal antibody designated as SK-9 was prepared as described (Du et al., *Arch. Biochem. Biophys.*, 2003;417:96-104) and coupled to Affi-Gel 10 according to the manufacturer's recommendation. Recombinant human TFPI-2 was purified from HEK 293 serum-free conditioned media by a two-step chromatography procedure involving heparin-agarose (Sprecher et al., *Proc. Natl. Acad. Sci. USA.*, 1994;91: 3353-3357) and SK-9-AffiGel 10 affinity chromatography. In the latter procedure, heparin-agarose purified TFPI-2 was dialyzed against 50 mM Tris-HCl (pH 7.5) and applied to the SK-9-AffiGel 10 column equilibrated at room temperature with this buffer. After a wash step with 50 mM Tris-HCl (pH 7.5)/0.5 M NaCl, TFPI-2 was eluted with 0.1 M glycine (pH 2.5)/0.5 M NaCl into one-tenth volume of 1 M Tris-HCl (pH 8.8) to immediately neutralize the pH 2.5 glycine. Recombinant TFPI-$2^{1-188}$ was expressed in stably-transfected HEK 293 cells and purified from the HEK 293 serum-free conditioned media by a combination of SP-Sepharose chromatography and SK-9-Affi-Gel10 immunoaffinity chromatography as described above. Recombinant R24K KD1 and R24Q KD1 were prepared as previously described (Schmidt et al., *J Biol. Chem.*, 2005;280: 27832-27838). Recombinant R24K KD 1-CT was expressed in *E. coli* and purified as described for R24K KD1 (Schmidt et al., *J Biol. Chem.*, 2005;280:27832-27838).

Treatments of HT-1080 Cells with Recombinant Proteins

HT-1080 cells were grown in six-well plates under standard conditions. At confluence, the cells were treated with fresh medium containing either wild-type TFPI-2, TFPI-$2^{1-188}$, R24Q KD1, R24K KD1, or R24K KD1-CT as previously described (Kempaiah and Kisiel, *Apoptosis*, 2008;13: 702-715). Briefly, duplicate wells were treated with purified proteins (1 μM final concentration) and incubated at either 37° C. or 4° C. for different time periods. Two wells were also treated with phosphate-buffered saline (PBS) at each temperature to serve as a control. At selected time points, the media was removed and the cells were rinsed once with PBS. The cells were then washed with 1 M NaCl/PBS for 30 minutes with gentle shaking to dissociate cell surface-bound proteins (Iino et al., *Arterioscler. Thromb. Vasc. Biol.*, 1998; 18:40-46). Finally, the cells were rinsed once with PBS, trypsinized and harvested for the preparation of cell lysates and cell fractions.

Preparation of Cell Lysates and Cell Fractions

To prepare total cell lysates, 1-3×$10^6$ cells were lysed by sonication in 500 μl of lysis buffer containing of 125 mM Tris-HCl (pH 6.8), 2% SDS, 10% glycerol, 50 mM sodium phosphate, 1 mM phenylmethanesulphonylfluoride (PMSF) and protease inhibitor cocktail. The lysate was kept on ice for about 10 minutes, centrifuged for 15 minutes at 10,000×g at 4° C., and the supernatant recovered. To prepare nuclear and cytosolic fractions, approximately 2×$10^6$ cells were harvested and washed twice with cold PBS by centrifugation at 600×g in a Beckman J-6M/E centrifuge for seven minutes at 4° C. Five volumes of ice cold cytosolic buffer (10 mM Hepes pH 7.4, 0.33 M sucrose, 1 mM $MgCl_2$, 0.1% Triton X-100 and protease inhibitor cocktail) was added to the cells and incubated on ice for 15 minutes. The cytosolic fraction was collected by centrifugation at 900×g for five minutes at 4° C. The resulting undissolved pellet was washed twice with cytosolic buffer followed by centrifugation at 900×g for five minutes at 4° C. Finally, the resulting pellet was resuspended in five volumes of ice cold buffer containing 0.45 M NaCl in 10 mM Hepes (pH 7.4) and protease inhibitor cocktail. The suspension was incubated on ice for an additional 15 minutes to dissolve the nucleus, and subsequently centrifuged at 18,000×g for five minutes at 4° C. The resulting supernatant was collected as the nuclear extract. All samples were boiled for three minutes in the presence of 5% SDS and stored at −20° C. until use.

Immunoblot Analyses

The cell lysate, cytosol and nuclear fractions were subjected to SDS-PAGE using 4-20% polyacrylamide gradient gels. Following electrophoresis, the proteins were electrotransferred to nitrocellulose membranes and subsequently blocked with 5% blotting grade non-fat dry milk in Tris-buffered saline (TBS)/0.1% Tween-20 at room temperature for two hours. The membranes were then probed with specific antibodies dissolved in fresh blocking buffer. Immunoreactive proteins were identified using HRP-conjugated secondary antibodies and a chemiluminescent reagent system essentially as described (Kempaiah et al., *Mol. Cancer,* 2007;6:20). The integrity of the cytosolic and nuclear fractions was verified using anti-α-tubulin and anti-histone-H1 antibodies, respectively (Guo et al., *Am. J Physiol. Cell Physiol.,* 2007; 292:2095-2102).

Confocal Microscopy

The internalization of recombinant TFPI-2 in HT-1080 cells was assessed by confocal microscopy using a Zeiss LSM510-META microscope and Alexa Fluor 488-conjugated TFPI-2. Approximately 0.5 mg of recombinant TFPI-2 protein was labeled with Alexa Fluor 488 dye following the manufacturer's instructions. Alexa Fluor-conjugated protein (50 μg/ml) was added to two sets of HT-1080 cells that were grown to confluence in two-chamber culture slides and incubated either at 37° C. or 4° C. for different time periods. Cells were then washed twice with cold PBS and fixed with 4% paraformaldehyde solution for 15 minutes. The slides were further rinsed twice with cold PBS, treated with a drop of mounting medium containing 4',6-diamidino-2-phenylindole (DAPI), and covered with a coverslip for confocal microscopy.

In order to view the cellular localization of endogenously produced TFPI-2 either in endothelial cells or cells stably-transfected with human TFPI-2 and TFPI-2$^{1-188}$ cDNA, cells were grown in two-chamber culture slides as described above. Cells were rinsed twice with PBS and fixed in 4% parafolinaldehyde solution for 30 minutes at room temperature. Following three washes with PBS, cells were permeabilized in 0.1% Triton X-100 in PBS for 10 minutes and further rinsed three times with PBS. Cells were then blocked with 10% goat serum in PBS for one hour at room temperature and incubated for two hours at room temperature with 10 μg/ml of SK-9, a murine monoclonal antibody raised against TFPI-2 (Arepally et al. *Blood,* 2000;95:1533-1540). Cells were then washed with 1% goat serum in PBS three times for 10 minutes, and incubated with goat anti-mouse Alexa Fluor-555 (1:250) for an additional two hours at room temperature in the dark. Finally, the cells were washed five times with 1% goat serum in PBS for 15 minutes and a drop of mounting medium containing DAPI was added and covered with coverslip in preparation for confocal microscopy.

Co-Immunoprecipitation Assay

To identify the adapter protein(s) involved in transporting TFPI-2 to the nucleus, we performed co-immunoprecipitation studies using the PROFOUND co-immunoprecipitation kit and cell lysates derived from either vehicle-treated HT-1080 cells, TFPI-2-treated HT-1080 cells or HT-1080 cells overexpressing TFPI-2. Approximately 4.5×10$^6$ cells from each system were washed twice with PBS, and the lysates prepared in the presence of proteinase inhibitors using the mammalian protein extraction reagent provided in the kit. Complexes of importin-α and TFPI-2 were removed from the lysate by co-immunoprecipitation according to the manufacturer's instructions. In this procedure, antibodies specific for either importin-α or TFPI-2 (SK-9) were covalently linked at room temperature for 16 hours to an amine-reactive gel in coupling buffer (8 mM sodium phosphate/2 mM potassium phosphate/10 mM KCl/140 mM NaCl [pH 7.4]). Cell lysates from the above preparations were added to the antibody-coupled columns and incubated at 4° C. for 18 hours with gentle end-over-end mixing. The columns were then washed several times with coupling buffer containing 0.5 M NaCl to remove non-specifically bound proteins, and finally eluted with the elution buffer provided in the kit. The eluted immunoprecipitation complexes were neutralized with 1 M Tris-HCl (pH 8.8), treated with 0.2 volumes of the non-reduced SDS sample buffer (0.3 M Tris-HCl (pH 6.8)/5% SDS/50% glycerol), boiled for 5 minutes, and subjected to immunoblotting.

Densitometry Analysis

The relative intensity of the Western blot bands were quantified using QUANTISCAN software (Biosoft, Cambridge, U.K.). The intensities are reported in arbitrary units (A.U.) obtained by subtracting the background value from the corresponding band's mean value.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The invention claimed is:

1. An isolated polypeptide comprising a membrane transduction peptide of human tissue factor pathway inhibitor-2 (TFPI-2), wherein the membrane transduction peptide consists of:
   amino acids 191-211 of SEQ ID NO:1, or a fragment thereof, possessing membrane transduction activity, wherein the said fragment comprises amino acids 191-195 of SEQ ID NO:1 or amino acids 206-211 of SEQ ID NO:1.

2. The isolated polypeptide of claim 1, wherein said fragment comprises amino acids 191-195 of SEQ ID NO:1.

3. The isolated polypeptide of claim 1, wherein said fragment comprises amino acids 206-211 of SEQ ID NO:1.

4. An isolated polypeptide comprising:
   a membrane transduction domain comprising a membrane transduction peptide of human tissue factor pathway inhibitor-2 (TFPI-2), wherein the membrane transduction peptide consists of amino acids 191-211 of SEQ ID NO:1, or a fragment thereof, possessing that possesses membrane transduction activity, wherein the at least a portion of amino acids 191-211 of SEQ ID NO:1 comprises amino acids 191-195 of SEQ ID NO:1 or amino acids 206-211 of SEQ ID NO:1; and
   a heterologous polypeptide domain.

5. A composition comprising an isolated polypeptide of claim 1 coupled to an active agent.

6. The composition of claim 5 wherein the active agent comprises a drug, a fluorophore, or a biological material.

7. The composition of claim 5 further comprising a pharmaceutically acceptable carrier.

8. A composition comprising an isolated polypeptide of claim 4 coupled to an active agent.

9. The composition of claim 8 wherein the active agent comprises a drug, a fluorophore, or a biological material.

10. The composition of claim 8 further comprising a pharmaceutically acceptable carrier.

11. A method of delivering a material to a target cell, the method comprising:
   providing a composition comprising: the material coupled to a membrane transduction domain, wherein the membrane transduction domain consists of amino acids 191-211 of SEQ ID NO:1, or a fragment thereof, posessing membrane transduction activity, wherein said fragment comprises amino acids 191-195 of SEQ ID NO:1 or amino acids 206-211 of SEQ ID NO:1; and
   contacting the composition with the target cell under conditions effective to permit the target cell to internalize the composition.

12. The method of claim 11, wherein said fragment comprises amino acids 191-198 of SEQ ID NO:1.

13. The method of claim 11, wherein said fragment comprises amino acids 198-211 of SEQ ID NO:1.

14. The method of claim 11, wherein said fragment comprises amino acids 191-195 of SEQ ID NO:1.

15. The method of claim 11, wherein said fragment comprises amino acids 206-211 of SEQ ID NO:1.

16. The method of claim 11 wherein contacting the composition with the target cell delivers the composition to the cell cytoplasm.

17. The method of claim 11 wherein contacting the composition with the target cell delivers the composition to the cell nucleus.

18. The method of claim 11 wherein the material comprises an active agent.

19. The method of claim 18 wherein the active agent comprises a drug, a fluorophore, or a nucleic acid.

20. The method of claim 18 wherein the active agent comprises a biological material.

21. The method of claim 16 wherein the biological material comprises a polypeptide, a nucleic acid, or a liposome.

22. The method of claim 11 wherein the composition comprises a nanoparticle.

* * * * *

UNITED STATES PATENT AND TRADEMARK OFFICE
CERTIFICATE OF CORRECTION

PATENT NO. : 8,324,344 B2  
APPLICATION NO. : 13/129942  
DATED : December 4, 2012  
INVENTOR(S) : Walter Kisiel Page 1 of 1

It is certified that error appears in the above-identified patent and that said Letters Patent is hereby corrected as shown below:

Column 23, Line 20  
Delete "that possesses"

Column 23, Lines 21 and 22  
Delete "the at least a portion of amino acids 191-211 of SEQ ID NO:1"  
and  
Insert --said fragment--

Signed and Sealed this  
Twelfth Day of February, 2013

Teresa Stanek Rea  
*Acting Director of the United States Patent and Trademark Office*